US010813346B2

(12) United States Patent
Wahl et al.

(10) Patent No.: US 10,813,346 B2
(45) Date of Patent: *Oct. 27, 2020

(54) ENHANCED IMMUNOGLOBULIN DIVERSITY

(71) Applicant: Trianni, Inc, San Francisco, CA (US)

(72) Inventors: Matthias Wahl, San Francisco, CA (US); Bao Duong, San Francisco, CA (US); Nigel Killeen, San Francisco, CA (US)

(73) Assignee: TRIANNI, INC., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/781,025

(22) PCT Filed: Nov. 30, 2016

(86) PCT No.: PCT/US2016/064237
§ 371 (c)(1),
(2) Date: Jun. 1, 2018

(87) PCT Pub. No.: WO2017/095939
PCT Pub. Date: Jun. 8, 2017

(65) Prior Publication Data
US 2019/0053474 A1 Feb. 21, 2019

Related U.S. Application Data

(60) Provisional application No. 62/262,757, filed on Dec. 3, 2015.

(51) Int. Cl.
*A01K 67/027* (2006.01)
*C07K 16/00* (2006.01)
*C12N 15/85* (2006.01)
*C12N 5/12* (2006.01)
*C12N 15/11* (2006.01)

(52) U.S. Cl.
CPC .......... *A01K 67/0278* (2013.01); *C07K 16/00* (2013.01); *C12N 5/12* (2013.01); *C12N 15/11* (2013.01); *C12N 15/85* (2013.01); *A01K 2217/072* (2013.01); *A01K 2227/105* (2013.01); *A01K 2267/01* (2013.01); *A01K 2267/03* (2013.01); *C07K 2317/52* (2013.01); *C07K 2317/60* (2013.01)

(58) Field of Classification Search
CPC ................................................. A01K 67/0278
See application file for complete search history.

(56) References Cited

U.S. PATENT DOCUMENTS

| | | | |
|---|---|---|---|
| 4,892,824 A | 1/1990 | Skaletsky |
| 5,591,669 A | 1/1997 | Krimpenfort et al. |
| 5,593,598 A | 1/1997 | McGinness et al. |
| 5,612,205 A | 3/1997 | Kay et al. |
| 5,633,425 A | 5/1997 | Lonberg et al. |
| 5,661,016 A | 8/1997 | Lonberg et al. |
| 5,789,215 A | 8/1998 | Berns et al. |
| 5,789,650 A | 8/1998 | Lonberg et al. |
| 5,814,318 A | 9/1998 | Lonberg et al. |
| 5,874,299 A | 2/1999 | Lonberg et al. |
| 5,877,397 A | 3/1999 | Lonberg et al. |
| 5,939,598 A | 8/1999 | Kucherlapati et al. |
| 5,985,615 A | 11/1999 | Jakobovits et al. |
| 6,023,010 A | 2/2000 | Krimpenfort et al. |
| 6,091,001 A | 7/2000 | Jakobovits et al. |
| 6,114,598 A | 9/2000 | Kucherlapati et al. |
| 6,130,364 A | 10/2000 | Jakobovits et al. |
| 6,162,963 A | 12/2000 | Kucherlapati et al. |
| 6,492,575 B1 | 12/2002 | Wagner et al. |
| 6,570,061 B1 | 5/2003 | Rajewsky et al. |
| 6,586,251 B2 | 7/2003 | Economides et al. |
| 6,596,541 B2 | 7/2003 | Murphy et al. |
| 6,653,113 B1 | 11/2003 | Berns et al. |
| 6,673,986 B1 | 1/2004 | Kucherlapati et al. |
| 6,998,514 B2 | 2/2006 | Bruggemann |
| 7,041,870 B2 | 5/2006 | Tomizuka et al. |
| 7,041,871 B1 | 5/2006 | Lonberg et al. |
| 7,064,244 B2 | 6/2006 | Jakobovits et al. |
| 7,105,348 B2 | 9/2006 | Murphy et al. |
| 7,129,084 B2 | 10/2006 | Buelow et al. |
| 7,145,056 B2 | 12/2006 | Jakobovits et al. |
| 7,205,148 B2 | 4/2007 | Economides et al. |
| 7,294,754 B2 | 11/2007 | Poueymirou et al. |
| 7,473,557 B2 | 1/2009 | Economides et al. |
| 7,476,536 B2 | 1/2009 | Kuroiwa et al. |
| 7,501,552 B2 | 3/2009 | Lonberg et al. |
| 7,541,513 B2 | 6/2009 | Bruggeman et al. |
| 7,659,442 B2 | 2/2010 | Poueymirou et al. |
| 7,868,223 B2 | 1/2011 | Tomizuka et al. |
| 8,158,419 B2 | 4/2012 | Lonberg et al. |
| 8,232,449 B2 | 7/2012 | Tanamachi et al. |
| 8,293,480 B2 | 10/2012 | Lonberg et al. |
| 8,367,888 B2 | 2/2013 | Bruggemann et al. |
| 8,502,018 B2 | 8/2013 | Murphy et al. |
| 8,754,287 B2 | 6/2014 | MacDonald et al. |
| 9,012,717 B2 | 4/2015 | MacDonald et al. |

(Continued)

FOREIGN PATENT DOCUMENTS

CA 2089661 C 3/1992
EP 0817835 A1 1/1998

(Continued)

OTHER PUBLICATIONS

Garcia-Arocena D. (2014, The Jackson Laboratory, Same Mutation, Different Phenotype?) (Year: 2014).*

(Continued)

*Primary Examiner* — Thaian N. Ton
*Assistant Examiner* — David A. Montanari
(74) *Attorney, Agent, or Firm* — Medler Ferro Woodhouse & Mills, PLLC

(57) ABSTRACT

The invention provides compositions and methods for enhanced production of immunoglobulin diversity. Specifically, the invention provides compositions and methods for making accessible a B cell receptor repertoire that has not been culled by developmental tolerance mechanisms. The invention also provides transgenic animals, cells, and antibodies resulting from these compositions and methods.

12 Claims, 6 Drawing Sheets

Specification includes a Sequence Listing.

(56) References Cited

U.S. PATENT DOCUMENTS

| | | |
|---|---|---|
| 2003/0017534 A1 | 1/2003 | Buelow et al. |
| 2006/0015957 A1 | 1/2006 | Lonberg et al. |
| 2007/0061900 A1 | 3/2007 | Murphy et al. |
| 2009/0055943 A1 | 2/2009 | Economides et al. |
| 2009/0111126 A1 | 4/2009 | Akamatsu et al. |
| 2009/0136950 A1 | 5/2009 | Dubridge et al. |
| 2010/0317539 A1 | 12/2010 | Yu |
| 2011/0145937 A1 | 6/2011 | MacDonald et al. |
| 2011/0236378 A1 | 9/2011 | Green et al. |
| 2011/0258710 A1 | 10/2011 | Murphy et al. |
| 2011/0283376 A1 | 11/2011 | Murphy et al. |
| 2012/0047585 A1 | 2/2012 | Rohrer et al. |
| 2012/0073004 A1 | 3/2012 | MacDonald et al. |
| 2012/0090041 A1 | 4/2012 | Buelow |
| 2012/0096572 A1 | 4/2012 | MacDonald et al. |
| 2013/0137101 A1 | 5/2013 | Economides et al. |
| 2013/0219535 A1 | 8/2013 | Wabl et al. |
| 2013/0263292 A1 | 10/2013 | Liang et al. |
| 2013/0333057 A1 | 12/2013 | MacDonald et al. |
| 2014/0283153 A1 | 9/2014 | Killeen |
| 2015/0183820 A1 | 7/2015 | Honda et al. |
| 2017/0058052 A1 | 3/2017 | Wabl et al. |
| 2017/0218090 A1 | 8/2017 | Green et al. |
| 2017/0226162 A1 | 8/2017 | Killeen et al. |
| 2017/0303517 A1 | 10/2017 | Wabl |
| 2017/0306352 A1 | 10/2017 | Wabl |
| 2018/0230238 A1 | 8/2018 | Wabl et al. |

FOREIGN PATENT DOCUMENTS

| | | | |
|---|---|---|---|
| EP | 1399559 A2 | 3/2004 | |
| EP | 1399575 A2 | 3/2004 | |
| EP | 2264163 A2 | 12/2010 | |
| EP | 2517556 A2 | 10/2012 | |
| EP | 2517557 A2 | 10/2012 | |
| GB | 2398784 A | 9/2004 | |
| GB | 2561352 A | 10/2018 | |
| WO | 94/25585 A1 | 11/1994 | |
| WO | 96/40915 A2 | 12/1996 | |
| WO | 99/45962 A1 | 6/1999 | |
| WO | 01/09187 A2 | 2/2001 | |
| WO | 02/12437 A2 | 2/2002 | |
| WO | 02/066618 A1 | 8/2002 | |
| WO | 02/066630 A1 | 8/2002 | |
| WO | 2008/070367 A2 | 6/2008 | |
| WO | 2008/081197 A1 | 7/2008 | |
| WO | 2009/013620 A2 | 1/2009 | |
| WO | 2009/157771 A2 | 12/2009 | |
| WO | 2010/039900 A2 | 4/2010 | |
| WO | 2011/004192 A1 | 1/2011 | |
| WO | 2011/123708 A2 | 10/2011 | |
| WO | 2011/158009 A1 | 12/2011 | |
| WO | 2011/163311 A1 | 12/2011 | |
| WO | 2012/018610 A2 | 2/2012 | |
| WO | 2012/123949 A1 | 9/2012 | |
| WO | 2013/022782 A1 | 2/2013 | |
| WO | 2013/092720 A1 | 6/2013 | |
| WO | 2013/138681 A1 | 9/2013 | |
| WO | 2013/171505 A2 | 11/2013 | |
| WO | 2014/013075 A2 | 1/2014 | |
| WO | 2015/112790 A2 | 7/2015 | |
| WO | WO-2015112790 A2 * | 7/2015 | ......... A01K 67/0278 |
| WO | 2015/188141 A2 | 12/2015 | |
| WO | 2017/035252 A1 | 3/2017 | |
| WO | 2018/189520 A1 | 10/2018 | |

OTHER PUBLICATIONS

Heimain-Patterson et al. (2011, Amyotrophic Lateral Schlerosis, vol. 00, pp. 1-8) (Year: 2011).*

2004, Barthold S., Genetica, vol. 122, pp. 75-88 (Year: 2004).*

Tong et al. (2010, Nature, vol. 467(7312), pp. 211-213) (Year: 2010).*

Hong et al. (2012, Stem Cells and Development, vol. 21(9), pp. 1571-1586) (Year: 2012).*

Gunasekaran et al., "Enhancing Antibody Fc Heterodimer Formation through Electrostatic Steering Effects," *J Biol Chem* 285:19637-19646 (2010).

Liu et al., "A Novel Antibody Engineering Strategy for Making Monovalent Bispecific Heterodimeric IgG Antibodies by Electrostatic Steering Mechanism," *J Biol Chem* 290:7535-7362 (2015).

Ma et al., "DNA Synthesis, Assembly and Applications in Synthetic Biology," *Curr Opin Chem Biol* 16:260-267 (2012).

McLenachan et al., "Flow-cytometric analysis of mouse embryonic stem cell lipofection using small and large DNA constructs," *Genomics* 89:708-720 (2007).

Rajewsky et al., "Allelic exclusion model questioned," Scientific Correspondence, *Nature* 359:371-372 (1992).

Sonoda et al, "B Cell Development under the Condition of Allelic Inclusion," *Immunity* 6:225-233 (1997).

Vetterman et al., "Allelic exclusion of immunoglobulin genes: models and mechanisms," *Immunol Rev* 237:22-42 (2010).

Wabl et al., "Allelic exclusion model questioned," Scientific Correspondence, *Nature* 359:370-371 (1992).

Altschul et al., "Basic local alignment search tool," *J Mol Biol* 215:403-410 (1990).

Avitahl et al., "A 125 bp region of the Ig $V_H1$ promoter is sufficient to confer lymphocyte-specific expression in transgenic mice," *Int Immunol* 8(9):1359-1366 (1996).

Bentley et al., "Unrearranged immunoglobulin variable region genes have a functional promoter," *Nucleic Acids Res* 10:1841-1856 (1982).

Berman et al., "Content and organization of the human Ig $V_H$ locus: definition of three new $V_H$ families and linkage to the Ig $C_H$ locus," *EMBO J* 7(3):727-738 (1988).

Blankenstein et al., "Immunoglobulin $V_H$ region genes of the mouse are organized in overlapping cluster," *Eur J Immunol* 17:1351-1357 (1987).

Brekke et al., "Assembly and analysis of the mouse immunoglobulin kappa gene sequence," *Immunogenetics* 56:490-505 (2004).

Bruggemann, "The Preparation of Human Antibodies from Mice Harbouring Human Immunoglobulin Loci," *Transgenic Animals: Generation and Use*, pp. 397-402, Ed. L.M. Houdebine, CRC Press (1997).

Casellas et al., "Igk allelic inclusion is a consequence of receptor editing," *J Exp Med* 204(1):153-160 (2007).

Cesari et al, "Elk-1 knock-out mice engineered by Flp recombinase-mediated cassette exchange," *Genesis* 38:87-92 (2004).

Church et al., "Lineage-specific biology revealed by a finished genome assembly of the mouse," *PLoS Biol* 7:e1000112 (2009).

Clarke et al., "An immunoglobulin promoter region is unaltered by DNA rearrangement and somatic mutation during B-cell development," *Nucleic Acids Res* 10:7731-7749 (1982).

de Bono et al., "$V_H$ Gene Segments in the Mouse and Human Genomes," *J Mol Biol* 342:131-143 (2004).

Decaire et al., "A Publicly Available PCR Methods Laboratory Manual and Supporting Material," *J Microbiol Biol Educ* 16:269-270 (2015).

Downing et al., "Technical assessment of the first 20 years of research using mouse embryonic stem cell lines," *Stem Cells* 22:1168-1180 (2004).

Doyen et al., "Analysis of promoter and enhancer cell type specificities and the regulation of immunoglobulin gene expression," *Gene* 50:321-331 (1986).

Featherstone et al., "The Mouse Immunoglobulin Heavy Chain V-D Intergenic Sequence Contains Insulators That May Regulate Ordered V(D)J Recombination," *J Biol Chem* 285:9327-9338 (2010).

Fishwild et al., "High-avidity human IgG kappa monoclonal antibodies from a novel strain of minilocus transgenic mice," *Nat Biotechnol*, 14:845-851 (1996).

Gellert, "Molecular analysis of V(D)J recombination," *Annu Rev Genet* 26:425-446 (1992).

Gopal et al., "Contribution of promoter to tissue-specific expression of the mouse immunoglobulin kappa gene," *Science* 229:1102-1104 (1985).

(56) References Cited

OTHER PUBLICATIONS

Hengartner et al., "Assignment of genes for immunoglobulin kappa and heavy chains to chromosomes 6 and 12 in mouse," *Proc Natl Acad Sci USA* 75:4494-4498 (1978).
Honjo et al., ed. *Immunoglobulin Genes*. San Diego, CA: Academic Press Inc., 1989; Chapters 4-6 and 17.
Ichihara et al., "Organization of human immunoglobulin heavy chain diversity gene loci," *Embo J* 7(13):4141-4150 (1988).
International Human Genome Sequencing Consortium, "Finishing the euchromatic sequence of the human genome," *Nature* 431:931-945 (2004).
Johnston et al., "Complete Sequence Assembly and Characterization of the C57BL/6 Mouse Ig Heavy Chain V Region," *J Immunol* 176:4221-4234 (2006).
Jones et al., "Replacing the complementarity-determining regions in a human antibody with those from a amouse," *Nature* 321:522-525 (1986).
Jung et al., "Unraveling V(D)J Recombination: Insights into Gene Regulation," *Cell* 116:299-311 (2004).
Kabat et al., "Variable region genes for the immunoglobulin framework are assembled from small segments of DNA—A hypothesis," *Proc Natl Acad Sci USA* 75:2429-2433 (1978).
Kabat et al., "Evidence supporting somatic assembly of the DNA segments (minigenes), coding for the framework, and complementarity-determining segments of immunoglobulin variable regions," *J Exp Med* 149:1299-1313 (1979).
Kawasaki et al., "One-Megabase Sequence Analysis of the Human Immunoglobulin λ Gene Locus," *Genome Res* 7:250-261 (1997).
Kitamura et al., "Targeted disruption of μ chain membrane exon causes loss of heavy-chain allelic exclusion," *Nature* 356:154-156 (1992).
Kozak, "An analysis of 5'-noncoding sequences from 699 vertebrate messenger RNAs," *Nucleic Acids Res* 15:8125-8148 (1987).
Kurosawa et al., "Organization, Structure, and Assembly of Immunoglobulin Heavy Chain Diversity DNA Segments," *J Exp Med* 155:201-218 (1982).
Lander et al., "Initial sequencing and analysis of the human genome," *Nature* 2001, 409:860-921 (2001).
Landsteiner et al., "On the Specificity of Serological Reactions with Simple Chemical Compounds (Inhibition Reactions)," *J Exp Med* 54:295-305 (1931).
Lee et al., "Genome data mining for everyone," *BMB Reports* 41(11):757-764 (2008).
Lefranc et al., "IMGT unique numbering for immunoglobulin and T cell receptor variable domains and Ig superfamily V-like domains," *Dev Comp Immunol* 27:55-77 (2003).
Lutz et al., "Pro-B cells sense productive immunoglobulin heavy chain rearrangement irrespective of polypeptide production," *Proc Nat Acad Sci USA* 108(26):10644-10649 (2011).
Mason et al., "Transcription cell type specificity is conferred by an immunoglobulin VH gene promoter that includes a functional consensus sequence," *Cell* 41:479-487 (1985).
Matsuda et al., "The Complete Nucleotide Sequence of the Human Immunoglobulin Heavy Chain Variable Region Locus," *J Exp Med* 188(11):2151-2162 (1998).
Misra et al., "Gene targeting in the mouse: advances in introduction of transgenes into the genome by homologous recombination," *Endocrine* 19:229-238 (2002).
Mouse Genome Sequencing Consortium, "Initial sequencing and comparative analysis of the mouse genome," *Nature* 420:520-562 (2002).
Ristevski, "Making better transgenic models: conditional, temporal, and spatial approaches," *Mol Biotechnol* 29:153-163 (2005).
Roebroek et al., "Mutant Lrp1 knock-in mice generated by recombinase-mediated cassette exchange reveal differential importance of the NPXY motifs in the intracellular domain of LRP1 for normal fetal development," *Mol Cell Biol* 26:605-616 (2006).
Saiki et al., "Analysis of enzymatically amplified beta-globin and HLA-DQ alpha DNA with allele-specific oligonucleotide probes," *Nature* 324:163-166 (1986).

Sakano et al., "Identification and nucleotide sequence of a diversity DNA segment (D) of immunoglobulin heavy-chain genes," *Nature* 290:562-565 (1981).
Schellenberg et al., "Pre-mRNA splicing: a complex picture in higher definition," *Trends Biochem Sci* 33:243-246 (2008).
Sharon, "The invariant tryptophan in an H chain V region is not essential to antibody binding," *J Immunol* 140:2666-2669 (1988).
Tonegawa, "Somatic generation of antibody diversity," *Nature* 302:575-581 (1983).
Toor et al., "Structural insights into RNA splicing," *Curr Opin Struct Biol* 19:260-266 (2009).
Venter et al., "The sequence of the human genome," *Science* 291:1304-1351 (2001).
Von Heijne, "Protein targeting signals," *Curr Opin Cell Biol* 2:604-608 (1990).
Wallace et al., "Manipulating the Mouse Genome to Engineer Precise Functional Syntenic Replacements with Human Sequence," *Cell* 128:197-209 (2007).
Xiong et al., "Chemical gene synthesis: strategies, softwares, error corrections, and applications," *FEMS Microbiol Rev* 32:522-540 (2008).
Zhang et al., "A New and Robust Method of Tethering IgG Surrogate Antigens on Lipid Bilayer Membranes to Facilitate the TIRFM Based Live Cell and Single Molecule Imaging Experiments," *PLOS One* 8(5):e63735 (2013).
Barthold, "Genetically altered mice: phenotypes, no phenotypes, and Faux phenotypes," *Genetica* 122: 75-88 (2004).
Brevini et al., "No shortcuts to pig embryonic stem cells," *Theriogenology* 74: 544-550 (2010).
Buta et al., "Reconsidering pluripotency tests: Do we sill need teratoma assays?" *Stem Cell Research* 11: 552-562 (2013).
Choe et al., "Fc-Binding Ligands of Immunoglobulin G: An Overview of High Affinity Proteins and Peptides," *Materials* 9: 994 (2016).
Garcia-Arocena, "Same Mutation, Different Phenotype?" The Jackson Laboratory, Blog Post dated Nov. 11, 2014. Accessed at https://www.jax.org/news-and-insights/jax-blog/2014/november/same-mutation-different-phenotype.
Gomez et al., "Derivation of cat embryonic stem-like cells from in vitro-produced blastocytes on homologous and heterologous feeder cells," *Theriogenology* 74: 498-515 (2010).
Heiman-Patterson et al., "Effect of genetic background on phenotype variability in transgenic mouse models of amyotrophic lateral sclerosis: A window of opportunity in the search for genetic modifiers," *Amyotrophic Laterla Sclerosis* 00: 1-8 (2011).
Hong et al., "Derivation and Characterization of Embryonic Stem Cell Lines Derived from Transgenic Fischer 344 and Dark Agouti Rats," *Stem Cells and Development* 21(9): 1571-1586 (2012).
Ivics et al., "Germline transgenesis in rodents by pronuclear microinjection of *Sleeping Beauty* transposons," *Nature Protocols* 9(4); 773-793 (2014).
Kontermann et al., "Bispecific antibodies," *Drug Discov Today* 20(7):838-847 (2015).
Meng et al., "Optimized production of transgenic buffalo embryos and offspring by cytoplasmic zygote injection," *Journal of Animal Science and Biotechnology* 6: 44 (2015).
Munoz et al., "Conventional pluripotency markers are unspecific for bovine embryonic-derived cell-lines," *Theriogenology* 69: 1159-1164 (2008).
Paris et al., "Equine embryos and embryonic stem cells: Defining reliable markers of pluripotency," *Theriogenology* 74: 516-524 (2010).
Tong et al., "Production of p53 gene knockout rats by homologous recombination in embryonic stem cells," *Nature* 467: 211-215 (2010).
Van Keuren et al., "Generating Transgenic Mice from Bacterial Artificial Chromosomes: Transgenesis Efficiency, Integration and Expression Outcomes," *Transgenic Research* 18(5): 769-785 (2009).
West et al., "Genome Editing in Large Animals," *Journal of Equine Veterinary Science* 41: 1-6 (2014).

(56) References Cited

OTHER PUBLICATIONS

Clargo et al., "The rapid generation of recombinant functional monoclonal antibodies from individual, antigen-specific bone marrow-derived plasma cells isolated using a novel fluorescence-based method," *mAbs* 6(1): 143-159 (2013).

Li et al., "Biochemical Analysis of the Regulatory T Cell Protein Lymphocyte Activation Gene-3 (LAG-3; CD223)," *Journal of Immunology* 173: 6806-6812 (2004).

Manz et al., "Analysis and sorting of live cells according to secreted molecules relocated to a cell-surface affinity matrix," *Proceedings of the National Academy of Science USA* 92: 1921-1925 (1995).

Pinder et al., "Isolation and Characterization of Antigen-Specific Plasmablasts Using a Novel Flow Cytometry-Based Ig Capture Assay," *Journal of Immunology* 199(12): 4180-4188 (2017).

Price et al., "Engineered cell surface expression of membrane immunoglobulin as a means to identify monoclonal antibody-secreting hybridomas," *Journal of Immunological Methods* 343: 28-41 (2009).

Extended European Search Report dated Jun. 5, 2019 in corresponding European Patent Application No. 16 871 431.9.

Verkoczy, Laurent et al., "Human Ig knockin mice to study the development and regulation of HIV-1 broadly neutralizing antibodies", Immunological Reviews, Jan. 1, 2017, vol. 275, No. 1, pp. 89-107.

Zhou, Hongzhe et al., "Generation of Monoclonal Antibodies against Highly Conserved Antigens", PLOS One, Jun. 30, 2009, vol. 4, No. 6.

\* cited by examiner

ENHANCED IMMUNOGLOBULIN DIVERSITY

CROSS-REFERENCE TO RELATED APPLICATIONS

The present application claims priority to U.S. Ser. No. 62/262,757, filed 3 Dec. 2015.

FIELD OF THE INVENTION

This invention relates to production of immunoglobulin molecules, including reactivating productive immunoglobulin rearrangements that may have been eliminated or edited due to reactivity with self antigens.

BACKGROUND OF THE INVENTION

In the following discussion certain articles and methods are described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Antibodies have emerged as important biological pharmaceuticals (i) because of their exquisite binding properties that can target antigens of diverse molecular forms, (ii) because they are physiological molecules with desirable pharmacokinetics that make them well tolerated in treated individuals, and (iii) because they are associated with powerful immunological properties that naturally ward off infectious agents. Furthermore, established technologies exist for the rapid isolation of antibodies from laboratory animals, which can readily mount a specific antibody response against virtually any foreign substance not present natively in the body.

In humans as well as most vertebrate animals, antibodies exist as dimers of two identical heavy (H) chains that are each paired with an identical light (L) chain. The N-termini of both H and L chains consist of a variable domain ($V_H$ and $V_L$, respectively) that together provide the H-L pair with its unique antigen-binding specificity. The exons that encode the antibody $V_H$ and $V_L$ domains do not exist in the germline DNA. Instead, each $V_H$ exon is generated by the recombination of randomly selected V, D, and J genes present in the H chain locus; likewise, individual $V_L$ exons are produced by the chromosomal rearrangements of randomly selected V and J genes in the light chain locus. The human genome contains two alleles that can express the H chain (one allele from each parent), two alleles that can express the kappa ($\kappa$) L chain, and two alleles that can express the lambda ($\lambda$) L chain. There are multiple V, D, and J genes at the H chain locus as well as multiple V and J genes at both L chain loci. Downstream of the J genes at each immunoglobulin locus exists one or more exons that encode the constant region of the antibody. In the heavy chain locus, exons for the expression of different antibody classes (isotypes) also exist.

During B cell development, gene rearrangements occur first on one of the two homologous chromosomes that contain the H chain genes. The resultant $V_H$ exon is subsequently spliced at the RNA level to the exons that encode the constant region of the H chain ($C_H$). A full-length H chain can now be expressed only if the $V_H$ exon formed following VDJ gene rearrangement is in frame with the $C_H$ exons. Upon successful completion of a VDJ exon for the production of a full-length H chain, surrogate light chains are then paired with the H chain homodimers to form a pre-B cell receptor (pre-BCR). Only B cells expressing a pre-BCR that can traffic to the cell surface and signal move on to recombine the V and J genes for L chain expression. In both humans and mice, the $\kappa$ L chain locus tends to rearrange before the $\lambda$ L chain locus. The VJ rearrangements occur on one L chain allele at a time until a functional L chain is produced, after which the L chain polypeptides can associate with the H chain homodimers to form a fully functional B cell receptor (BCR).

FIG. 1 illustrates typical gene arrangements found in the heavy chain locus of most animals including humans. In this figure, the presence of multiple V (103) and D (104) genes on both heavy chain alleles (101 and 102) is compressed and denoted by "n" so as to emphasize the structure of the constant region locales of the chromosomes. The heavy chain intronic enhancer (106) is present downstream of the J genes (105). C$\mu$ and C$\delta$ (108) encoding IgM and IgD, respectively, are the first isotypes to be expressed by B cells. The $C_H$ exons encoding other antibody classes (109-114) exist further downstream. In the C57BL/6 mouse strain, these are C$\gamma$3 (109), C$\gamma$1 (110), C$\gamma$2b (111), C$\gamma$2c (112), Cc (113), and Ca (114). Certain mouse strains such as BALB/c have C$\gamma$2a instead of C$\gamma$2c. An isotype switch region (107) is present preceding the first $C_H$ exon of each antibody class except for C$\delta$.

Although the antibody diversity that each organism can generate from the combined permutations of H chain VDJ and L chain VJ gene rearrangements is quite vast, it is nevertheless limited by the mechanisms that remove antibodies with binding specificity for self antigens.

In healthy animals including humans, developing progenitor B cells with receptors specific for self antigens are normally induced to undergo secondary light chain VJ gene rearrangements—a process called receptor editing. When receptor editing still fails to remove the self reactivities, the autoreactive B cells are induced to undergo apoptosis or anergy. It has been estimated that 25-75% of all developing B cells are lost per individual organism to these processes of self tolerance. Though such culling of autoreactive B cells is clearly necessary to prevent autoimmune diseases, the lost repertoire is likely to be of significant benefit for the isolation of therapeutic antibodies, particularly those with binding specificities for epitopes that are highly conserved among species. Catalytic sites of enzymes and receptor-ligand interaction interfaces are examples of such conserved epitopes that may be the preferred targets for pharmaceutical intervention.

To bypass these tolerance mechanisms, antibody engineers have resorted to non-physiological methods, such as yeast and phage displays, to generate antibodies that would have been eliminated due to their reactivity with self antigens in an intact organism. In addition to various formatting issues, such methods also suffer from inefficiency at generating high affinity antibodies of qualities comparable to those produced by affinity maturation—the physiological process of multiple rounds of somatic hypermutation and selection. Thus, a method for more efficient production of antibodies to highly conserved epitopes is an important unmet need. The methods and compositions provided by the present specification meet this important need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention provides compositions and methods to reactivate immunoglobulin rearrangements in B cells that may have been eliminated or edited by normal tolerance mechanisms. Under physiological conditions, tolerance mechanisms remove B cells that express a BCR, composed of immunoglobulin heavy and light chains, with autoreactive properties. The culled repertoire constitutes about 25-75% of total antigen receptors made by the developing B cells. Among those culled are antigen receptors with binding specificities to highly conserved epitopes, which are often the preferred targets for therapeutic intervention.

The present invention provides processes for enhanced production of immunoglobulin diversity. Specifically, the invention comprises methods and compositions for making accessible a BCR repertoire that has not been directly culled by the developmental tolerance mechanisms. Preserving this otherwise lost repertoire facilitates the isolation of therapeutic antibodies, particularly those with specificities for epitopes that are highly conserved among species.

In one embodiment, the invention comprises a genetically engineered animal. The B cells in this animal express a diverse antigen receptor repertoire that has been shaped in an essentially normal fashion by tolerance mechanisms. Crucially, however, the B cells from this animal also carry a latent repertoire that has not been subjected to any developmental selection, and that can be expressed in place of, or in addition to, the normal repertoire in an inducible fashion. The isolated antibodies from this hidden alternative repertoire include those of efficacious value for therapeutic purposes, most notably antibodies that are specific for highly conserved epitopes. In another embodiment, the invention comprises methods for creating such genetically engineered animals.

Thus, the present invention provides a genetically modified animal comprising an immunoglobulin heavy chain allele that can undergo productive VDJ rearrangement but is deficient in expression of a functional immunoglobulin heavy chain from the immunoglobulin heavy chain allele, wherein the deficiency in expression can be corrected to allow for production of a functional immunoglobulin heavy chain that has not been subjected to selection by tolerance mechanisms. In one embodiment of the invention, the immunoglobulin heavy chain allele in the genetically modified animal is modified such that an in-frame VDJ rearrangement is disabled for allelic exclusion but preserved for expression in an inducible manner. In one aspect, one or more changes are introduced to the immunoglobulin heavy chain allele in the genetically modified animal such that a functional heavy chain cannot be expressed efficiently at an immature stage of B cell development following a productive VDJ rearrangement. In yet another aspect, one or more changes are introduced to the immunoglobulin heavy chain allele in the genetically modified animal to allow for inducible expression of a productively rearranged VDJ exon that was not previously expressed as part of a functional heavy chain during an immature stage of B cell development.

Yet another embodiment of the present invention provides an immunoglobulin heavy chain gene from a genetically modified animal, wherein part or all of one or more heavy chain constant region exons are placed in inverted reading frame orientation relative to rearranged VDJ exon on the same chromosome. In some aspects of this embodiment, the immunoglobulin heavy chain gene is a functional heavy chain that can be expressed from a productively rearranged VDJ exon in or following the presence of a recombinase, DNA-modifying protein, or transcriptional regulator.

Another embodiment of the present invention provides an immunoglobulin heavy chain gene from a genetically modified animal, wherein a DNA element is inserted to suppress or prevent expression of a functional heavy chain during an immature stage of B cell development. In some configurations, after suppression or prevented expression a functional heavy chain is then expressed from a productively rearranged VDJ exon in or following the presence of a recombinase, DNA-modifying protein, or transcriptional regulator.

The present invention also provides primary B cells, immortalized B cells, or hybridomas derived from a genetically modified animal, wherein a VDJ exon is expressed from an immunoglobulin gene of the invention. Additionally, the present invention encompasses a part or whole immunoglobulin protein expressed from the VDJ exon derived from the primary B cells, immortalized B cells, or hybridomas of the present invention.

Yet another embodiment of the invention provides a genetically modified animal comprising an immunoglobulin light chain allele that can undergo productive VJ rearrangement but is deficient in expression of a functional immunoglobulin light chain from the immunoglobulin light chain allele, wherein the deficiency in expression can be corrected to allow for production of a functional immunoglobulin light chain that has not been subjected to selection by tolerance mechanisms. In some aspects, the immunoglobulin light chain allele is modified such that an in-frame VJ rearrangement is disabled for allelic exclusion but preserved for expression in an inducible manner. In yet other aspects, one or more changes are introduced to the immunoglobulin light chain allele such that a functional light chain cannot be expressed efficiently at an immature stage of B cell development following a productive VJ rearrangement. In other aspects, one or more changes are introduced to the immunoglobulin light chain allele to allow for inducible expression of a productively rearranged VJ exon that has not been previously expressed as part of a functional light chain during an immature stage of B cell development.

The present invention also provides an immunoglobulin light chain gene from a genetically modified animal, wherein part or all of the light chain constant region exon is placed in inverted reading frame orientation relative to rearranged VJ exon on the same chromosome. In some aspects, a functional light chain can then be expressed from a productively rearranged VJ exon in or following the presence of a recombinase, DNA-modifying protein, or transcriptional regulator.

Additionally, in one aspect the present invention provides an immunoglobulin light chain gene from a genetically modified animal, wherein a DNA element is inserted to suppress or prevent expression of a functional light chain during an immature stage of B cell development. In one configuration, a functional light chain can be expressed from a productively rearranged VJ exon in or following the presence of a recombinase, DNA-modifying protein, or transcriptional regulator.

The present invention further provides primary B cells, immortalized B cells, or hybridomas derived from a genetically modified animal, wherein a VJ exon is expressed from the immunoglobulin genes of the present invention. In addition, the invention provides part or whole immunoglobulin protein expressed from the VJ exon derived from the primary B cells, immortalized B cells, or hybridomas of the invention.

In another embodiment, the present invention provides a method for producing a genetically modified animal, comprising the step of modifying a first immunoglobulin allele in the animal such that an in-frame VDJ or VJ rearrangement is disabled for allelic exclusion but preserved for expression in an inducible manner. In some aspects, the modifying step comprises rendering the modified immunoglobulin allele deficient in cell surface expression; deficient in antigen receptor assembly; deficient in antigen receptor signaling; or deficient in pre-B cell receptor signaling; in other aspects, the modifying step comprises alternating expression of one immunoglobulin allele to another immunoglobulin allele within the same cell in an inducible fashion; and in yet other aspects, the modifying step comprises replacing a full-length heavy or light chain immunoglobulin gene in the first immunoglobulin allele with an open-reading frame that confers selection for productive in-frame VDJ or VJ rearrangement.

Some aspects of the methods of the present invention provide a method of generating a transgenic animal that produces antibodies of interest comprising: modifying a first endogenous heavy chain allele, wherein some or all of the exons comprising the constant domains are flanked by oppositely oriented site-specific recognition sequences for site-specific recombination; modifying a second endogenous heavy chain allele, wherein certain constant domain exons are placed in antisense orientation with respect to transcriptional direction and are flanked by oppositely oriented site-specific recognition sequences for site-specific recombination; allowing VDJ rearrangements and production of B cells; allowing developing B cells to mature and exit the bone marrow; inducing site-specific recombination of the first and second engineered heavy chain alleles; and immunizing the transgenic animal with an antigen of interest.

Other aspects provide a method of generating a transgenic animal that produces antibodies of interest comprising: modifying a first endogenous heavy chain allele, wherein the $C_H$ exons are flanked by two directly oriented site-specific recognition sequences; modifying a second endogenous heavy chain allele, wherein a DNA cassette expressing a gene necessary for B cell survival or functions is inserted downstream from the J genes in sense orientation and is flanked by two directly oriented site-specific recognition sequences, followed by another DNA cassette that expresses $C_H$ domains along with the same gene necessary for B cell survival or functions; allowing VDJ rearrangements and production of B cells; allowing developing B cells to mature and exit the bone marrow; inducing site-specific recombination of the first and second engineered heavy chain alleles; and immunizing the transgenic animal with an antigen of interest.

Other aspects of the methods of the present invention provide a method of generating a transgenic animal that produces antibodies of interest comprising: modifying a first endogenous heavy chain allele, wherein a DNA cassette flanked by two oppositely oriented site-specific recognition sequences is inserted downstream from the J genes in antisense orientation with respect to transcriptional direction; modifying a second endogenous heavy chain allele, wherein a DNA cassette flanked by two oppositely oriented site-specific recognition sequences is inserted downstream from the J genes in sense orientation with respect to transcriptional direction; allowing VDJ rearrangements and production of B cells; allowing developing B cells to mature and exit the bone marrow; inducing site-specific recombination of the first and second engineered heavy chain alleles; and immunizing the transgenic animal with an antigen of interest.

Yet other aspects of the methods of the present invention provide a method of generating a transgenic animal that produces antibodies of interest comprising: modifying a first endogenous heavy chain allele, wherein a pre-assembled VDJ exon is inserted where J genes normally reside and a DNA cassette flanked by two directly oriented site-specific recognition sites is inserted in sense orientation downstream of the pre-assembled VDJ exon; modifying a second endogenous heavy chain allele, wherein a DNA cassette expressing a selection marker is inserted downstream of the J genes in sense orientation; allowing VDJ rearrangements and production of B cells; allowing developing B cells to mature and exit the bone marrow; inducing site-specific recombination of the first and second engineered heavy chain alleles; and immunizing the transgenic animal with an antigen of interest.

The same methods, of course, also could be used to generate the light chain versions of the invention; that is, light chain rearrangements that may have been eliminated or edited due to tolerance mechanisms.

Other embodiments and aspects of the invention are described in detail infra.

DEFINITIONS

Figure 1:
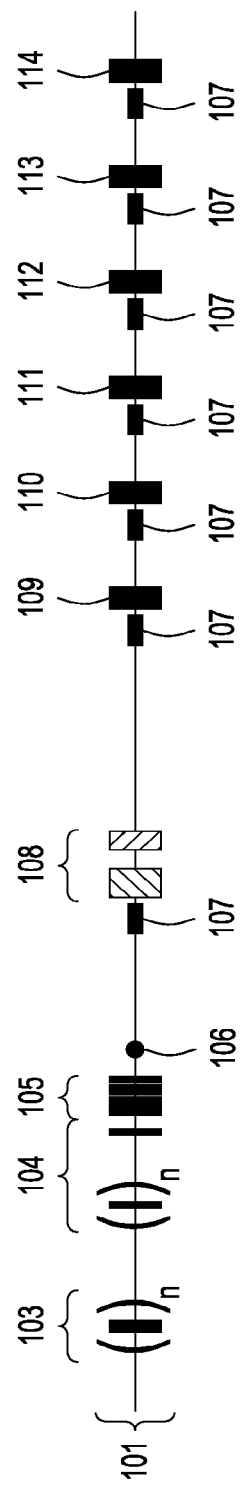
FIG. 1 is a simple depiction of immunoglobulin genes in the heavy chain locus.
Figure 1:
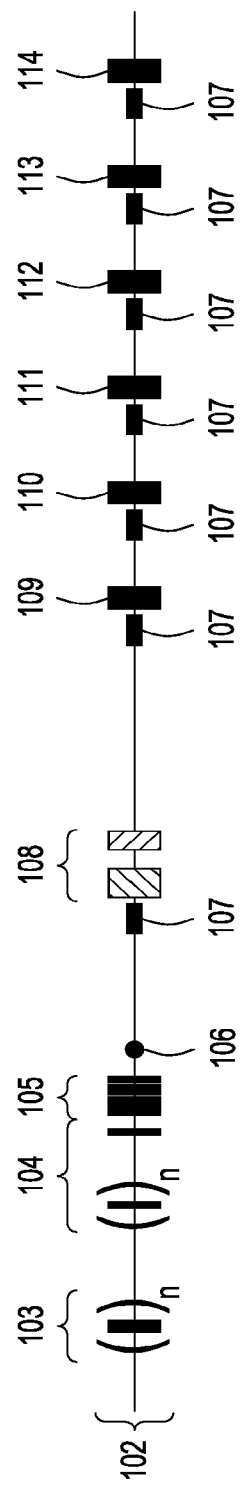

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "transgene" is used herein to describe genetic material which has been or is about to be artificially inserted into the genome of a cell, and particularly a cell of a vertebrate host animal.

"Transgenic animal" refers to a non-human animal, usually a mammal such as a rodent, particularly a mouse or rat although other animals are envisioned, having an exogenous nucleic acid sequence present as a chromosomal or extra-chromosomal element in a portion of its cells or stably integrated into its germ-line DNA (i.e., in the genomic sequence of most or all of its cells).

A "recombinase" is an enzyme that catalyzes the excision and joining of DNA segments. The recombinases used in the methods herein can be delivered to a cell via a transgene that is integrated into the heavy chain locus or at any other chromosomal site. In some embodiments, the recombinase proteins are expressed upon demand using an inducible promoter or a promoter derived from a developmentally regulated gene, such as CD21 or CD23, that is expressed only at certain stages of B cell development.

"Site-specific recombination" refers to the excision of DNA at a particular sequence on one or more DNA strands, followed by the joining of two DNA ends either in cis or trans, by a recombinase enzyme, such as Cre. Certain site-specific recombination systems can be used to specifically delete, invert, or insert DNA, with the precise event controlled by the nucleotide composition of the specific sites, the orientation of the specific sites, and the type of recombinase enzymes expressed.

"Recognition sequences" are particular sequences of nucleotides that a protein, DNA, or RNA molecule, or combination thereof (such as, but not limited to, a restriction endonuclease, a modification methylase or a recombinase) recognizes and binds. For example, a recognition sequence for Cre recombinase is a stretch of DNA consisting of two 13 base-pair inverted repeats (serving as the recombinase binding sites) flanking an 8 base-pair core (see, e.g., Sauer, Current Opinion in Biotechnology, 5:521-527 (1994)). Multiple recognition sequences can exist for a particular recombinase. For example, loxP, lox66, and lox71 are all recognition sequences for Cre recombinase that differ only in the nucleotide composition of the 13 base-pair inverted repeats (see, e.g., Oberdoerffer, et al., Nucleic Acids Research, 31:e140 (2003)).

A "DNA-modifying protein" refers to an endogenous or exogenous enzyme, along with its cofactors and any other components, that is capable of introducing changes to the DNA or altering the transcriptional activity of a gene. Examples of a DNA-modifying protein include but are not limited to a DNA ligase, a DNA repair protein, a DNA polymerase, a methyltransferase, a nuclease, a phosphatase, a histone-modifying protein, and a histone-binding protein. Activation-induced cytidine deaminase (also known as AID or AICDA) involved in mediating isotype switching and somatic hypermutation is an example of a DNA-modifying protein.

"Cell surface" refers to the plasma membrane of the cell; i.e., that part of the cell most directly exposed to extracellular spaces and available for contact both with cells and proteins in the extracellular (including intercellular) space.

As used herein, "productive rearrangement" is a VDJ or VJ rearrangement that, upon transcription then translation, is in frame with the constant region domains. ("V(D)J" rearrangement or exon indicates either heavy chain VDJ rearrangement or light chain VJ rearrangement.) The variable domain of a heavy chain or light chain is considered "functional" if it can be expressed in-frame with the downstream constant region exons(s). A heavy chain or light chain protein translated from a productive VDJ or VJ rearrangement, respectively, is referred to as "functional" if it can be expressed as part of a pre-BCR, BCR, or secreted antibody.

An immunoglobulin "allele" described herein refers to a chromosome segment derived from the heavy chain or light chain locus that may include the variable gene segments, an intronic enhancer, constant regions genes, and other sequences of endogenous or exogenous origin, including recombinase recognition sequences and regulatory sequences such a promoter, polyadenylation signal, translation termination sequence, and the like.

"Allelic exclusion" refers to the fact that most B cells in vertebrate species such as rodents or humans carry a productively rearranged heavy chain gene, as well as light chain gene, on only one of the homologous autosomes.

A genomic "locale" is any region of the genome, typically a gene, which is associated with one particular functional aspect. The term locale is used here to refer to parts of immunoglobulin loci. For example, it can refer to that part of an immunoglobulin locus that primarily contains one kind of gene segment, such as a V gene segment locale, or a D gene segment locale, or a J gene segment locale, or more broadly, the variable locale, which includes all of the V, D and J gene segments. The constant region locale is that part of an immunoglobulin locus that contains constant region exons.

An "immature stage" of B cell development refers to an intermediate phase of B cell differentiation, during which a hematopoietic stem cell undergoes genetic programming to become a mature, yet antigen-inexperienced (or naïve), B cell. During the immature stages of B cell development, H and L chains expressed from the recombined VDJ and VJ exons, respectively, undergo several selection processes. Developing B cells that fail to express a functional pre-BCR or BCR on the cell surface are eliminated due to lack of survival signals from the pre-BCR or BCR. Additionally, developing B cells that express B cell receptors with specificity for self antigens are normally induced to undergo receptor editing or apoptosis during, or shortly after, the final immature stage of development. Allelic exclusion, a process by which developing B cells are prevented from expressing more than one functional heavy chain VDJ or light chain VJ exon per cell, also occurs during the immature stages of B cell development. In adult mammals, including humans and mice, B cells normally develop in the bone marrow and exit the bone marrow to complete the final stages of development.

A "mature" B cell refers to an antigen-inexperienced (naïve) B cell, which is capable of clonal expansion, as well as differentiation into a memory cell or an antibody-secreting cell, during an antigenic response. In adult mammals, including humans and mice, developing B cells reach the "mature stage" of development after they have exited the bone marrow. Mature naïve B cells exist as at least three subpopulations outside of the bone marrow; two predominant subpopulations stably express CD21 and/or CD23.

DETAILED DESCRIPTION OF THE INVENTION

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999) *Genome Analysis: A Laboratory Manual Series* (Vols. I-IV); Weiner, Gabriel, Stephens, Eds. (2007), *Genetic Variation: A Laboratory*

*Manual*; Dieffenbach, Dveksler, Eds. (2007), *PCR Primer: A Laboratory Manual*; Sambrook and Russell (2006), *Condensed Protocols from Molecular Cloning: A Laboratory Manual*; and Green and Sambrook (2012), *Molecular Cloning: A Laboratory Manual* (all from Cold Spring Harbor Laboratory Press); Stryer, L. (1995) *Biochemistry* (4th Ed.) W.H. Freeman, New York N.Y.; Lehninger, *Principles of Biochemistry* 3rd Ed., W. H. Freeman Pub., New York, N.Y.; and Berg et al. (2002) *Biochemistry,* 5th Ed., W.H. Freeman Pub., New York, N.Y.; Nagy, et al., Eds. (2003) *Manipulating the Mouse Embryo: A Laboratory Manual* (3rd Ed.) Cold Spring Harbor Laboratory Press, Cold Spring Harbor, N.Y., *Immunology Methods Manual* (Lefkovits ed., Academic Press 1997); *Gene Therapy Techniques, Applications and Regulations From Laboratory to Clinic* (Meager, ed., John Wiley & Sons 1999); M. Giacca, *Gene Therapy* (Springer 2010); *Gene Therapy Protocols* (LeDoux, ed., Springer 2008); *Cell and Tissue Culture: Laboratory Procedures in Biotechnology* (Doyle & Griffiths, eds., John Wiley & Sons 1998); and *Mammalian Chromosome Engineering—Methods and Protocols* (G. Hadlaczky, ed., Humana Press 2011), all of which are herein incorporated in their entirety by reference for all purposes.

Note that as used herein and in the appended claims, the singular forms "a," "an," and "the" include plural referents unless the context clearly dictates otherwise. Thus, for example, reference to "an immunoglobulin" refers to one or more such immunoglobulins, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

The Invention in General

A major purpose of this invention is to create a means to facilitate the isolation of antibodies specific for epitopes that are highly conserved among species by reactivating productive immunoglobulin rearrangements that may have been otherwise eliminated or culled due to reactivity with self antigens (i.e., due to normal tolerance mechanisms).

Gene conservation between related species is an expected consequence of Darwinian selection against the loss of certain biological functions that are necessary for the organism's survival or reproductive fitness. The conserved genes and other genetic elements may encode non-messenger RNA molecules, gene regulatory elements, or messenger RNA molecules that are in turn translated into proteins. This process of natural selection tends to protect essential proteins from diversifying extensively during evolution at the level of amino acid sequence and/or structure. Such sequence and/or structural conservation can be readily observed in cell lines as well as in transgenic animals, wherein human proteins often can functionally replace those of endogenous non-human origins. Human cytokines, for example, can activate the orthologous receptors on mouse cell lines. The conserved functionality associated with these protein sequences or structures make them ideal targets for pharmaceutical intervention.

Although antibodies can be the ideal molecular therapeutics to target such conserved epitopes, developing antibodies against such conserved epitopes has been a challenge. Because by definition the conserved epitopes are also present as self antigens in the body, physiological tolerance mechanisms normally purge the B cell repertoire of those receptors that can recognize these conserved epitopes. As many as 75% of all newly developed B cells in an individual organism are purged by tolerance mechanisms.

The present invention overcomes this last limitation and, for the purposes of antibody discovery, makes available antibody repertoires that have not been directly shaped by tolerance. By preserving the otherwise purged B cell repertoires, the invention facilitates the isolation of antibodies specific for epitopes that are normally difficult to raise antibodies against, particularly those that are also present as self.

In certain embodiments, the invention implements modifications to the immunoglobulin alleles such that an in-frame VDJ or VJ rearrangement on one allele is disabled for allelic exclusion but preserved for expression at a mature B cell developmental stage. Such modifications accomplish one or more of the following: (i) one of the rearranged alleles is deficient in cell surface expression, antigen receptor assembly, or participating in antigen receptor (or pre-B cell receptor) signaling; (ii) the expression of one immunoglobulin allele can be alternated to the other allele in an inducible fashion; (iii) in place of a full-length heavy or light chain, one of the immunoglobulin alleles expresses an open-reading frame that confers selection for productive in-frame V(D)J rearrangement on the same chromosome.

In one embodiment, a transgenic animal such as a transgenic mouse carries engineered heavy chain alleles on both chromosomes, where modifications are introduced in the heavy chain locales that normally express the constant domains. In this embodiment, one of the two engineered alleles is capable of undergoing VDJ rearrangements to create heavy chain diversity during B cell development, but is unable to express full-length heavy chains. The other engineered allele is capable of expressing full-length heavy chain proteins necessary to support B cell development and survival.

In some aspects of this embodiment, one or both engineered alleles also carry recognition sequences (wild-type or mutated) for one or more site-specific recombinases such as Cre or Flp. The recognition sites are placed in such a way that site-specific recombination changes the functionality of the constant domain-encoding part of the locus. That is, if the allele is capable of expressing a fully functional heavy chain protein, then site-specific recombination deprives the locus of this property. Similarly, if the allele is incapable of expressing a fully functional heavy chain protein, then site-specific recombination confers the ability to express a functional heavy chain on the locus.

The site-specific recombinase-mediated changes just summarized are accomplished either by deleting or inverting pieces of DNA in the constant domain-encoding part of the heavy chain locus on the two homologous chromosomes. In certain aspects of this embodiment, site-specific recombinase-dependent loss of constant domain full functionality on one chromosome is accompanied by synchronous, or near synchronous, gain of full functionality on the other chromosome. In a favored aspect, expression of this site-specific recombinase is under the control of a promoter derived from a gene, such as CD21 or CD23, that is expressed after B cells have exited the bone marrow and matured in the periphery. In another aspect, the site-specific recombinase is under the control of an inducible promoter, such as one that is induced by tamoxifen or doxycycline (see, e.g., Saunders, Methods in Molecular Biology, 693:103-115 (2011)).

After the heavy chain constant domain functionality is switched from one chromosome to the other via site-specific recombination, the allele that has been previously disabled for full-length heavy chain expression now gains this functionality. The newly emerged heavy chains can now be expressed on the cell surface and participate in clonal expansion in response to the antigen used in immunization. Crucially, the repertoire of these newly emerged heavy chains has not been shaped by B cell tolerance mechanisms.

The light chains are expressed from independent VJ rearrangements at the immunoglobulin κ or λ locus. Although the light chain repertoire has been subjected to tolerance mechanisms along with that of the previously expressed heavy chains, each antibody generated from the pairing of newly emerged heavy chains with pre-existing light chains is expected to acquire new antigen binding specificity.

Subsequent to the induced site-specific recombinase-dependent switch just described, transgenic mice are immunized with an antigen. Clonal expansion in response to the antigen should depend mostly on the antibodies comprised of heavy chains encoded by the second allele; i.e., the one that gains constant domain functionality due to the induced site-specific recombinase event. Repeated immunizations may be employed to maximize clonal expansion and antigen-specific antibody diversity. After the immunization regimen has been completed, hybridoma or other standard techniques may be employed to isolate B cells specific for the immunogen.

In another embodiment of the invention, the light chain repertoire rather than that of the heavy chain is preserved from being purged by B cell tolerance mechanisms. Conceptually similar to the compositions and methods of the preceding embodiment, versions of the invention in this embodiment also feature transgenic animals, such as transgenic mice, carrying engineered immunoglobulin alleles at the κ and/or λ light chain locus/loci, wherein modifications are introduced in the locales that normally express the constant domains. The engineered alleles are capable of undergoing VJ rearrangements to create light chain diversity during B cell development. On one chromosome, the engineered allele is capable of expressing full-length light chains, while the engineered allele on the other chromosome is disabled in this regard. A site-specific recombinase system is employed to allow the previously hidden VJ rearrangement to be expressed with the downstream constant domains. The newly emerged light chains can now participate in an immune response during immunization without being first subjected to tolerance mechanisms.

In addition to the embodiments described in detail herein, one of ordinary skill in the art could employ other methods to reactivate B cell receptor repertoires that may have been susceptible to tolerance mechanisms, e.g., such as employing CRISPR/CAS genome editing tools or transcription control mechanisms such as, e.g., repressor proteins and sequences.

A further important consideration about this invention is that while the elimination of tolerance is expected to permit the isolation of antibodies specific for self proteins and highly conserved proteins or parts of proteins, it is also expected to provide a broadened antibody repertoire in general. Such a broadened repertoire may prove useful for the isolation of antibodies specific for non-conserved epitopes if, for example, such antibodies are normally depleted from the repertoire due to cross-reactivity with self proteins. Cross-reactivity in one species does not necessarily predict similar cross-reactivity in another, so it is possible that antibodies of this sort may prove to be useful therapeutics in humans even if they demonstrate an unwanted pattern of reactivity in another species.

Transgenic Cell Libraries

The transgenic cells of the invention may be used to produce expression libraries, preferably low complexity libraries, for identification of antibodies of interest. The present invention thus also includes antibody libraries produced using the cell technologies of the invention for identification of antigen-specific antibodies expressed by plasma cells.

Transgenic Animals

This invention provides transgenic animals carrying engineered heavy chain or light chain genes. In certain aspects of the embodiments, the transgenic animals of the invention further comprise human immunoglobulin regions. For example, numerous methods have been developed for replacing endogenous mouse immunoglobulin regions with human immunoglobulin sequences to create partially or fully human antibodies for drug discovery purposes. Examples of such mice include those described in, for example, U.S. Pat. Nos. 7,145,056; 7,064,244; 7,041,871; 6,673,986; 6,596,541; 6,570,061; 6,162,963; 6,130,364; 6,091,001; 6,023,010; 5,593,598; 5,877,397; 5,874,299; 5,814,318; 5,789,650; 5,661,016; 5,612,205; and 5,591,669.

In particularly favored aspects of the invention, the transgenic animals of the invention comprise chimeric immunoglobulin segments as described in co-pending application US Pub. No. 2013/0219535 by Wabl and Killeen. Such transgenic animals have a genome comprising an introduced partially human immunoglobulin region, where the introduced region comprises human variable region coding sequences and regulatory and non-coding variable sequences based on the endogenous genome of the non-human vertebrate. Preferably, the transgenic cells and animals of the invention have genomes in which part or all of the endogenous immunoglobulin region is removed.

Use in Antibody Production

Culturing cells in vitro has been the basis of the production of numerous therapeutic biotechnology products, and involves the production of protein products in cells and release into the support medium. The quantity and quality of protein production over time from the cells growing in culture depends on a number of factors, such as, for example, cell density, cell cycle phase, cellular biosynthesis rates of the proteins, condition of the medium used to support cell viability and growth, and the longevity of the cells in culture. (See, for example, Fresney, *Culture of Animal Cells*, Wiley, Blackwell (2010); and *Cell Culture*

*Technology for Pharmaceutical and Cell-Based Therapies*, Ozturk and Ha, Eds., CRC Press, (2006).)

EXAMPLES

The following are examples of the heavy chain versions of the invention.

The same strategies and methods, of course, also could be used to generate the light chain versions of the invention; that is, light chain rearrangements that may have been eliminated or edited due to tolerance mechanisms.

Example 1—Repertoire Preservation by Inversion of the $C_H$ Open Reading Frame

In this example, transgenic mice are generated to harbor two modified heavy chain alleles at the heavy chain locus. In one aspect of this embodiment, the modifications entail a first step, or steps, that result in deletion of all of the constant domain exons from the endogenous locus of the transgenic animal such as a mouse. Subsequently, engineered DNA is inserted into the endogenous locus at the site of the deletion (or close to it).

On one allele, one or more of the $C_H$ exons are placed in an inverted orientation relative to the transcriptional direction of the $V_H$ exon. As a consequence of the $C_H$ exon inversion, a productive VDJ rearrangement from this allele cannot support B cell development or allelic exclusion due to the lack of full-length heavy chain protein expression. The inverted $C_H$ exon(s) is/are also flanked by two oppositely oriented site-specific DNA recombination sequences, such as lox66 and lox71 (or other site-specific recombination sites), which can mediate inversion of the DNA contained therein when Cre is expressed (see, e.g., Oberdoerffer, et al., Nucleic Acids Research, 31:e140 (2003)).

On the other allele, the same $C_H$ exon(s) is/are left in the native transcriptional configuration, but is/are also flanked by the same oppositely oriented site-specific recombination sequences. However, all other $C_H$ exons are removed to prevent isotype switching. Full-length heavy chains can be expressed normally from a productive VDJ recombination on this allele. Despite the absence of isotype switching, this allele can support normal B cell development when a productive VDJ exon is formed.

In a favored aspect, the assembled VDJ genes on both heavy chain alleles are derived from individual gene segments comprising human coding sequences with mouse regulatory and other non-coding sequences and are described in the co-pending application US Pub. No. 2013/0219535 by Wabl and Killeen. All endogenous sequences downstream, including the heavy chain constant region genes, are described in LOCUS: NG_005838 (1 . . . 180, 971).

Transgenic mice carrying the modified heavy chain alleles are then bred with another transgenic mouse line that expresses, e.g., Cre recombinase. The expression of Cre is preferably under the control of a promoter belonging to a gene, such as CD21 or CD23, that is developmentally upregulated on B cells that have exited the bone marrow and matured in the periphery, but not yet further differentiated into antigen-experienced cells. When Cre is expressed, the $C_H$ domain-encoding DNA sequences flanked by lox66 and lox71 on both alleles are inverted. The heavy chain allele that has been previously expressing full-length heavy chains necessary to support B cell development and survival is now inactivated by the inversion of one or more of its $C_H$ exons. By contrast, the $V_H$ exon that has been previously prevented from full-length heavy chain expression—and therefore, hidden from tolerance mechanisms—can now generate fully functional heavy chains because the orientation of its $C_H$ exons has been rotated to be in the same transcriptional direction as the mRNA.

Following an immunization regimen, hybridoma or other cloning technology may be exploited to recover B cells with specificity for the immunogen.

Figure 2:
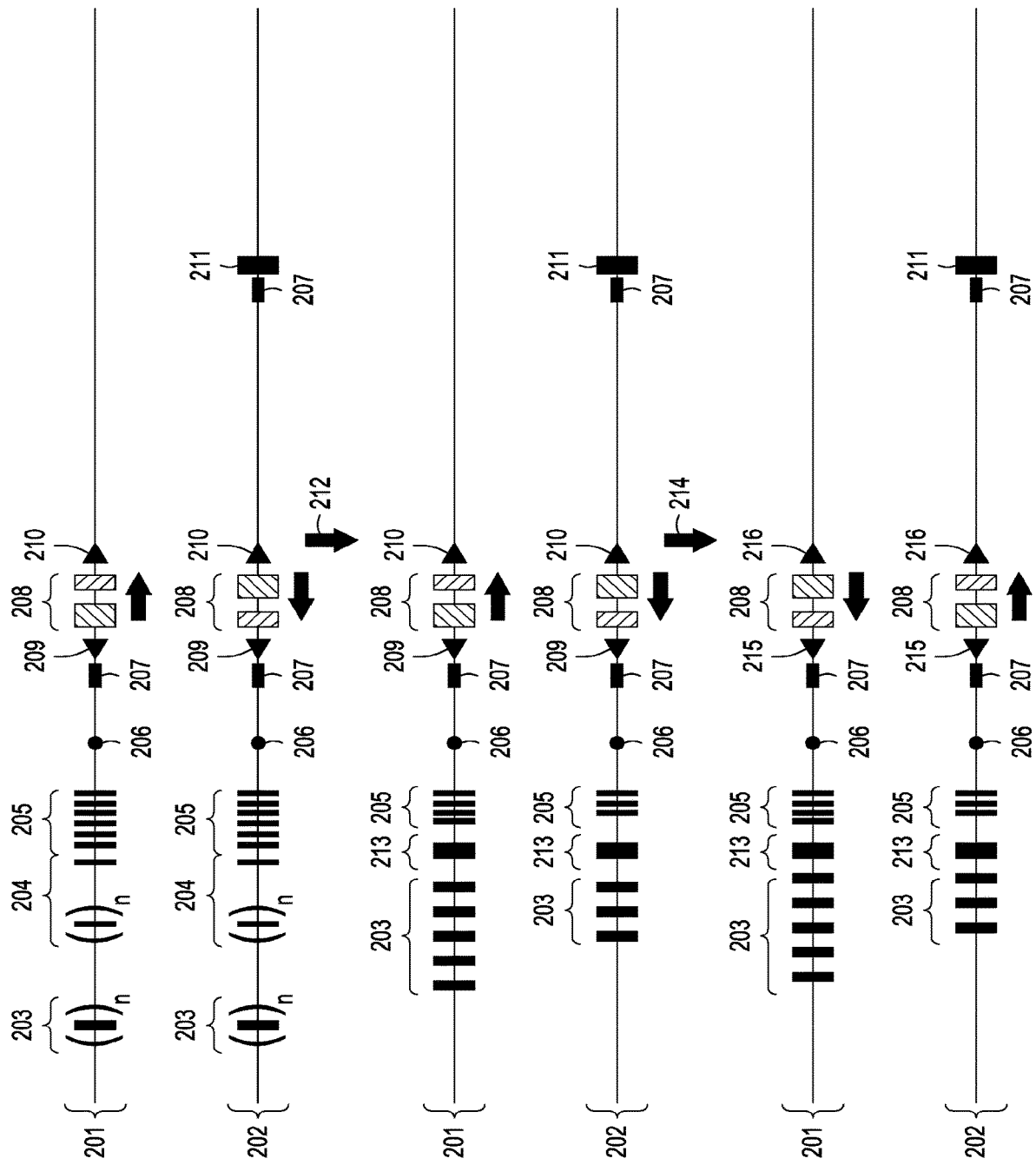
FIG. 2 depicts repertoire preservation of a heavy chain allele by inversion of the $C_H$-encoding open reading frame.

This exemplary configuration is depicted in FIG. 2. Shown are two heavy chain alleles (201, 202) containing multiple V (203), D (204), and J (205) genes upstream of a heavy chain intronic enhancer (206). The presence of multiple V (203) and D (204) genes is compressed and denoted by "n". On allele 201, part or all of the exons encoding Cµ and/or Cδ (208) are in the same sense orientation (arrow below) as the transcriptional direction of the heavy chain mRNA. By contrast, part or all of the Cµ and/or Cδ exons (208) on allele 202 are present in the reverse orientation (arrow below) relative to the mRNA transcriptional direction. The inverted Cµ and/or Cδ exons (208) on allele 202 are immediately flanked by two oppositely oriented recognition sequences (209, 210) for site-specific DNA recombination. On allele 201, the Cµ and/or Cδ exons (208) are also flanked by the same recognition sequences for site-specific DNA recombination (209, 210). All downstream endogenous $C_H$ exons encoding other antibody classes and their switch regions (207) are deleted from allele 201 to prevent isotype switching on this allele. Following VDJ rearrangements (212), even if the assembled $V_H$ exon (213) on allele 202 is productive, allele 202 is not capable of expressing full-length heavy chains as its Cµ and/or Cδ exons are in the antisense configuration. That is, normal B cell development is dependent on the productive VDJ rearrangement (213) and expression of functional heavy chains from allele 201. When expression of the site-specific DNA recombinase is induced after B cells have matured and exited the bone marrow (214), the DNA segments flanked by recognition sequences (209, 210) on both alleles undergo irreversible inversion because the resultant recombination sites (215, 216) are no longer competent for recombination. Allele 202 is now capable of expressing full-length heavy chains, while allele 201 becomes inactivated by the inversion of its $C_H$ exon(s). Following immunization with an antigen of interest, allele 202 can undergo normal B cell activation process including switching to downstream isotypes (211).

Example 2—Repertoire Preservation by Disruption of H Chain Open Reading Frame with a Gene Necessary for B Cell Development, Function, or Survival In this example, the heavy chain locus is modified by gene targeting and/or other procedures such as recombinase-mediated cassette exchange.

In one aspect of this embodiment, the modifications entail a first step, or steps, that result in deletion of all of the endogenous constant domain exons from the transgenic animal's heavy chain locus. Subsequently, engineered DNA is inserted into the locus at the site of the deletion (or close to it). The engineered DNA introduced into the heavy chain locus comprises the following major components (or components of a related functional nature): first an open reading frame—in mini-gene (i.e., comprised of exons and introns) or cDNA form—encoding a molecule that is essential for signaling and/or proper surface expression and function of the B cell antigen receptor (hereafter this essential molecule is referred to as "pB", and the open reading frame that encodes it as "orfB"); and second, an open reading frame—again in mini-gene or cDNA form—encoding a heavy chain constant domain (orfC).

Possible options for pB include, but are not limited to, CD79A or CD79B (otherwise known as Ig-alpha or Ig-beta, respectively).

Importantly, pB is necessary for the development of B cells from hematopoietic progenitor cells because this process is aborted if the pre-BCR or B cell antigen receptor does not reach the cell surface properly, or if it is impaired in its signaling capacity.

A preferred aspect of the modifications just described is that orfB is placed in an exon located downstream of the J genes in the heavy chain locus; i.e., in the location where the first available constant domain-encoding exon would normally be found. A further preferred aspect of the modifications is that orfB is preceded in-frame by a sequence encoding a ribosomal skip sequence of viral origin (commonly referred to as a "2A" peptide). The 2A-orfB contiguous open reading frame is placed in the exon such that, after splicing, it is also in-frame with upstream productively rearranged VDJ exons.

Because of the arrangement just described, expression of pB only occurs if the upstream open reading frame (VDJ) is productive. If a stop codon is present, or if the upstream reading frame is out of frame, then protein translation would either abort before the 2A-pB-encoding sequence is reached, or the wrong reading frame of the 2A-pB exon would be used and thus, pB would not be expressed.

In the context of a loss-of-function (preferably null) mutation in the endogenous gene encoding pB, the arrangement thus constitutes a selection for productive VDJ rearrangements. This follows from the necessary role that pB performs during B cell development as explained above, and the fact that without a productive VDJ rearrangement no pB is expressed.

A further preferred aspect of the modifications is inclusion of recognition sequences for a site-specific recombinase (or recombinases) such that the 2A-orfB unit can be excised in an inducible fashion. As a consequence of this excision event the downstream constant domain encoding sequence (orfC) is effectively moved into the location previously occupied by 2A-orfB. The excision therefore renders the locus capable of expression of an immunoglobulin heavy chain comprised of a productively rearranged VDJ and the constant domain encoded by orfC. Inclusion of a functional splice acceptor sequence at the 5' end is a necessary feature of orfC for this capability to be realized.

Excision of 2A-orfB occurs in the animal as a consequence of expression of the relevant site-specific recombinase in a developmental or differentiation stage-specific fashion, or in an inducible fashion.

The excision event just described causes loss of the upstream 2A-orfB from the locus, yet the protein product of orfB, i.e., pB, is essential for signaling and/or proper surface expression and function of the B cell antigen receptor. Thus, to retain full antigen receptor functionality, a further preferred aspect of the invention is inclusion of an additional copy of 2A-orfB immediately downstream of orfC. The requirement of 2A-orfB in this location is that it is placed in-frame with orfC without any intervening stop codons. An IRES-orfB unit placed in the 3' untranslated region downstream of orfC is an acceptable—but probably less preferred—alternative to 2A-orfB for this purpose.

In the form described, the modified heavy chain allele permits development of B cells only when pB is expressed subsequent to a productive VDJ rearrangement. Crucially, the upstream 2A-orfB unit does not include a constant domain-encoding open reading frame and thus the variable domain encoded by the rearranged locus is not available for expression on the cell surface as part of the pre-BCR or BCR.

Under normal circumstances, progenitor B cells undergo apoptosis at an early developmental stage if they do not gain expression of an immunoglobulin heavy chain. The above modifications to the heavy chain locus prevent expression of a full-length heavy chain protein (unless the described recombinase-mediated excision event has occurred). Thus, for B cells to avoid early developmental apoptosis, they must express a heavy chain protein from a different genomic source. One possible choice for this would be the heavy chain locus on the homologous chromosome. A preferred version of the invention, therefore, is an animal with a heterozygous heavy chain locus genotype: one allele modified as described above, and the other capable of developmental heavy chain expression. As an alternative to a heavy chain locus on the homologous chromosome, another genomic source for the heavy chain protein could be any ectopic transgenic or transposed heavy chain locus.

The requirement for heavy chain expression during B cell development is due to the involvement of the protein in a signaling process that promotes survival, mitosis and differentiation of precursor cells. Signaling depends on the assembly of a multi-chain antigen receptor complex and its release from the endoplasmic reticulum (ER). Immunoglobulin light chains displace the BiP chaperone protein from heavy chains thereby facilitating their passage out of the ER in nascent antigen receptor complexes. At early developmental stages surrogate light chains perform this role for pre-B cell receptors, whereas at later stages it is performed by κ or λ light chains for mature B cell receptors.

In one aspect of the invention involving the modified heavy chain locus described above, the engineered animal carries versions of the κ and λ loci in its genome that allow for normal or partially normal light chain diversity. Such loci are the source of immunoglobulin light chain proteins that allow for basal/tonic signaling necessary for B cell development and survival, and also, of course, antigen-dependent clonal expansion.

To summarize, as outlined above one possible preferred embodiment of the invention involves the following: a heterozygous heavy chain locus genotype comprised of the (2A-orfB)-orfC-2A-orfB heavy chain allele (with the parentheses used to denote the potential for conditional excision of 2A-orfB) balanced by an endogenous or transgenic heavy chain allele capable of developmental heavy chain expression; a null mutation in the endogenous gene encoding pB; normal, or partially normal, light chain diversity due to VJ rearrangement at endogenous or transgenic light chain loci; and restricted (post-developmental) expression of a site-specific recombinase that can cause excision of the upstream 2A-orfB unit from the (2A-orfB)-orfC-2A-orfB heavy chain allele.

As described, a preferred embodiment of the invention allows for expression of heavy chain proteins from the (2A-orfB)-orfC-2A-orfB heavy chain allele when the upstream 2A-orfB unit is excised from it as a consequence of site-specific recombination. B cells in which this event occurred would express two types of heavy chain proteins: one from each of the heavy chain alleles.

The present invention enables the production and isolation of antibodies that would normally be removed from the repertoire by developmental receptor editing or negative selection (i.e., "tolerance-free" antibodies). The embodiment of the invention described in this Example allows for this, albeit in the context of dual heavy chain expression in B cells. Excision of the upstream 2A-orfB unit from the (2A-orfB)-orfC-2A-orfB heavy chain allele is used to create a population of dual heavy chain-expressing B cells from which tolerance-free antibodies are isolated. This is accomplished by immunizing the animals with an antigen and subsequently isolating antibodies specific for the antigen using standard hybridoma or alternative technology.

An additional aspect of this embodiment of the invention involves adding a further component that substantially removes the dual heavy chain expression aspect. This aspect involves a site-specific recombinase-mediated alteration to the allele that expresses heavy chains during B cell development (i.e., not the (2A-orfB)-orfC-2A-orfB heavy chain allele). This alteration silences the allele and renders it incapable of heavy chain expression. In a preferred version of this aspect, the recombinase that mediates this alteration is the same one that causes excision of the upstream 2A-orfB unit from the (2A-orfB)-orfC-2A-orfB heavy chain allele. Thus, expression of the site-specific recombinase accomplishes two things, preferentially in a contemporaneous fashion in individual B cells: one is the induction of heavy chain expression from the (2A-orfB)-orfC-2A-orfB heavy chain allele by excision of the upstream 2A-orfB unit; while the other is the silencing of heavy chain expression from the balancing allele that is responsible for heavy chain expression during B cell development.

Gene targeting and/or other procedures such as recombinase-mediated cassette exchange are used to generate the heavy chain allele required for the refinement just outlined. As with the (2A-orfB)-orfC-2A-orfB heavy chain allele, the modifications necessary for the refinement are introduced in two or more steps. A first step, or steps, result in deletion of all of the constant domain-encoding exons from the endogenous heavy chain locus of the transgenic animal. Subsequently, engineered DNA is inserted into the locus at the site of the deletion (or close to it). The engineered DNA comprises the following major components (or components of a related functional nature): first an open reading frame—in mini-gene or cDNA form—encoding a heavy chain constant domain (orfC); and second, either upstream or downstream of orfC recognition sequences for a site-specific recombinase (or recombinases) such that orfC can be excised (or functionally inactivated by inversion) in an inducible fashion.

The refined heavy chain allele generated by this method can be functionally silenced by the action of the site-specific recombinase on the recognition sequences flanking orfC on this allele. Importantly, it is not essential for this orfC to be identical to the orfC present in the (2A-orfB)-orfC-2A-orfB allele. Whereas the latter must have sufficient functionality to allow for efficient immune responses, the only requirement for the refined allele is that it should encode heavy chains that are competent in signaling for B cell development. Thus, a preferred minimal version of orfC in this refined allele is a mini-gene or cDNA encoding a transmembrane form of the IgM constant domains.

In contrast to the minimal orfC just described, the preferred form of orfC in the (2A-orfB)-orfC-2A-orfB allele is more complex. Ideally, the form comprises two (or more) constant-domain encoding open reading frames, both of which are preceded by sequences that allow for class switch recombination. In this preferred form, the first open reading frame encodes the IgM constant domain, and the second one encodes an IgG constant domain. This arrangement is advantageous because it allows for identification of antigen-specific cells that have undergone class switch recombination from IgM to IgG, with such cells invariably being enriched for higher affinity antigen binding as a consequence of somatic hypermutation during germinal center reactions.

A downstream 2A-orfB unit is a necessary feature of the (2A-orfB)-orfC-2A-orfB heavy chain allele. In the class switch capable-version of the allele just outlined, this unit must be added in two places: at the end of both the IgM and IgG constant domain open reading frames. In this way, the pB protein is expressed from this allele before and after class switch recombination.

Figure 3:
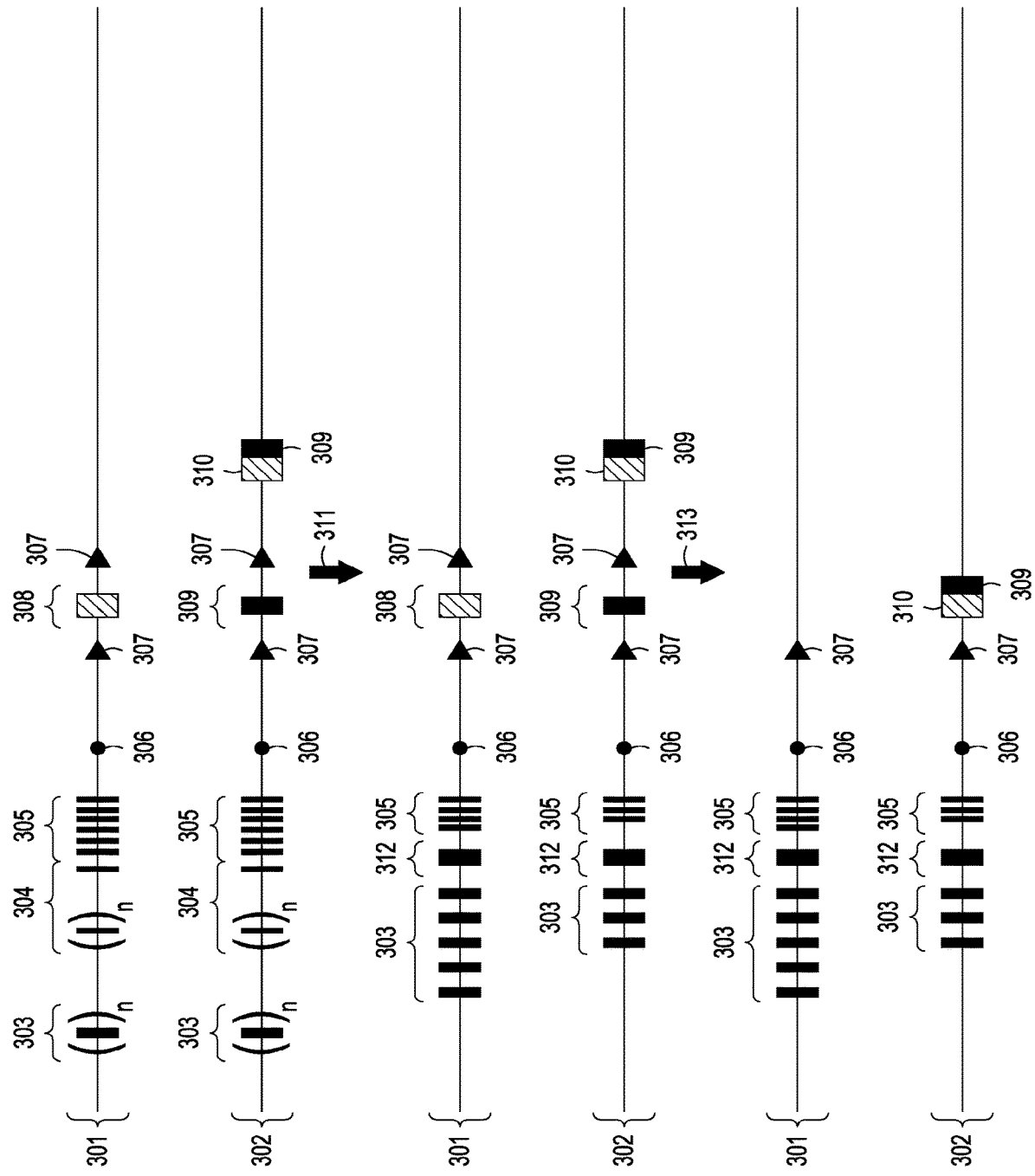
FIG. 3 depicts repertoire preservation of a heavy chain allele via disrupting the open reading frame with a gene necessary for B cell development, function, or survival.

This example of the invention is illustrated in FIG. 3. A modified heavy chain allele capable of full-length heavy chain expression is shown at 301. This heavy chain allele comprises arrays of V (303), D (304), and J genes (305) upstream of a heavy chain intronic enhancer (306) and an arrangement of constant domain exons for the expression of IgM or any other isotype (308) necessary to support B cell development. The presence of multiple V (303) and D (304) genes on both alleles is denoted by "n". The $C_H$ exons (308) are flanked by two directly oriented recognition sequences (307) for a site-specific recombinase. A version of the second modified heavy chain allele containing a (2A-orfB)-orfC-2AorfB element is shown at 302, with 307 depicting the sites recognized by a site-specific recombinase, 309 depicting 2A-orfB, and 310 depicting orfC. Following VDJ recombination events (311) on both alleles, an in-frame $V_H$ exon (312) on allele 301 is required for full-length heavy chain expression with the $C_H$ domains (308). Additionally, another in-frame VDJ exon (312) on allele 302 is required for the expression of a protein from element 309 that is indispensable for B cell development. Once the expression of a site-specific recombinase is induced (313), element 308 on allele 301 is deleted, causing this allele to become inactivated. At the same time, allele 302 becomes activated by the deletion of element 309.

In an alternative version of the embodiment, the requirement for two downstream copies of the 2A-orfB unit is obviated simply by removing this unit from its downstream location in the (2A-orfB)-orfC-2A-orfB allele and placing it instead in a downstream location on the other heavy chain allele (i.e., the allele that expresses heavy chains during B cell development and that is functionally silenced by site-specific recombination contemporaneously with excision of the upstream 2A-orfB unit from the (2A-orfB)-orfC-2A-orfB allele). The downstream location on this other allele is one that follows the constant domain-encoding open reading frame, which as described above—in its minimal form—encodes only the transmembrane form of the IgM constant domain. This downstream location comes after the downstream recognition sequence for the site-specific recombinase.

To summarize the above refinements: the (2A-orfB)-orfC-2A-orfB allele becomes instead a (2A-orfB)-orfC allele, wherein orfC is comprised of an IgM and an IgG open reading frame, both of which are preceded by sequences allowing for class switch recombination; the other heavy chain allele has an open reading frame encoding a transmembrane form of IgM flanked by recognition sequences for a site-specific recombinase (the same recombinase that causes excision of 2A-orfB from the (2A-orfB)-orfC allele) followed by a 2A-orfB unit in a downstream location. A key advantage of this combination of alleles is that sustained expression of pB requires contemporaneous site-specific recombination on both heavy chain alleles. This requirement effectively removes the possibility of dual heavy chain expression.

Figure 4:
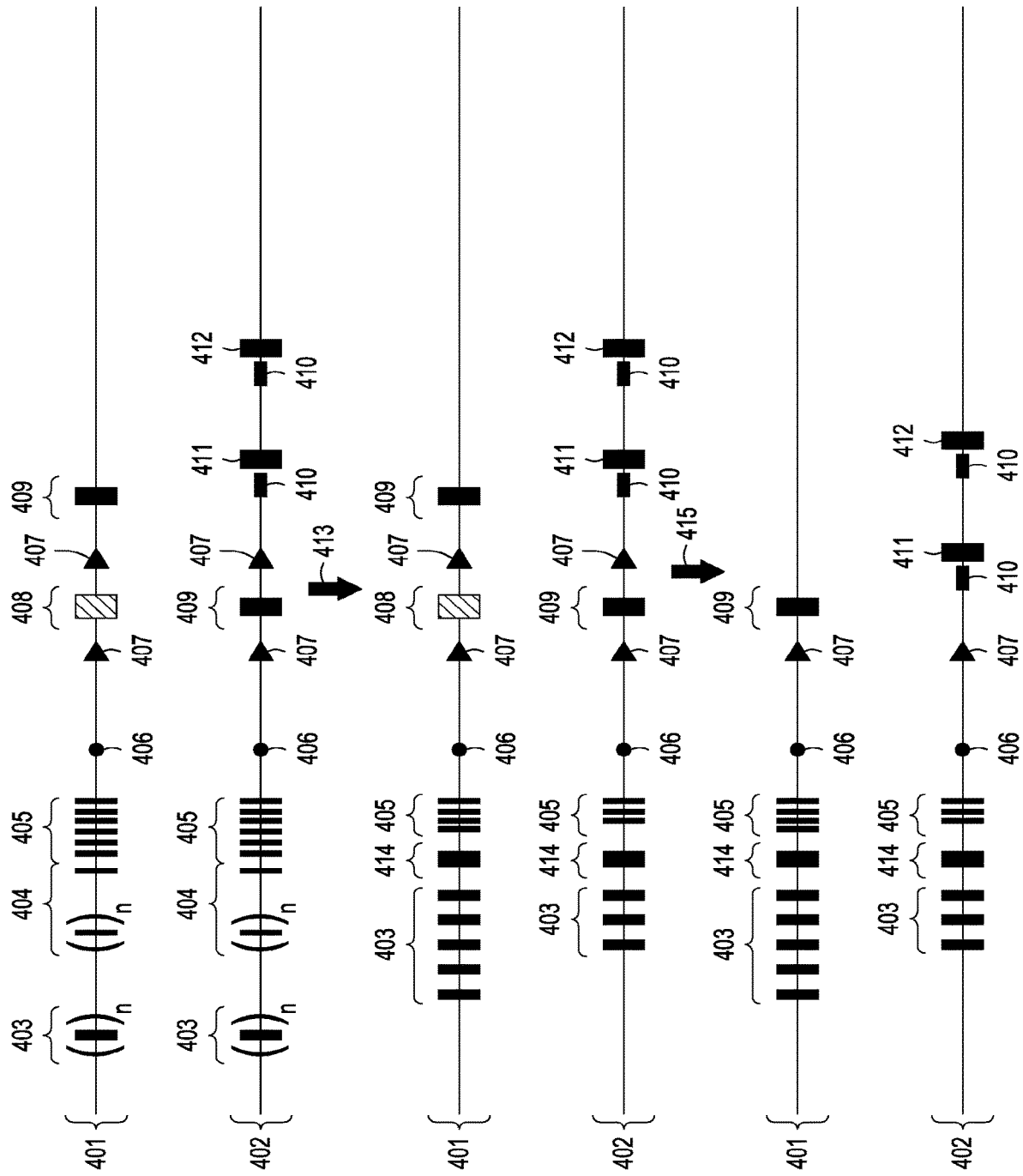
FIG. 4 depicts alternative heavy chain configurations to preserve the repertoire of a heavy chain allele via disruption of an open reading frame with a gene necessary for B cell development, functions, or survival.

This alternative aspect of the embodiment is depicted in FIG. 4. A modified heavy chain allele capable of full-length heavy chain expression is shown at 401. This heavy chain allele comprises arrays of V (403), D (404), and J genes (405) upstream of a heavy chain intronic enhancer (406), and an arrangement of constant domain exons for the expression of IgM or any other isotype (408) necessary to support B cell development. The presence of multiple V and D genes on both alleles is denoted by "n". The $C_H$ exons (408) are flanked by two directly oriented recognition sequences (407) for a site-specific recombinase. A 2A-orfB element (409) is present further downstream of the $C_H$ exons. A second modified heavy chain allele containing the (2A-orfB)-orfC element is shown at 402, with 407 depicting the sites recognized by a site-specific recombinase, 409 depicting 2A-orfB, and 410 depicting an isotype class switch region, 411 depicting an exon or collection of exons encoding a µ constant domain, 412 depicting a γ constant domain, and orfC comprising both the 410/411 unit and the 410/412 unit. Following VDJ recombination events (413) on both alleles, an in-frame $V_H$ exon (414) on allele 401 is required for full-length heavy chain expression with the $C_H$ domains (408). Additionally, another in-frame VDJ exon (414) on allele 402 is required for the expression of a protein from element 409 that is indispensable for B cell development. Once the expression of a site-specific recombinase is induced (415), element 408 on allele 401 is deleted, causing this allele to express orfB (409) in place of full-length heavy chains. At the same time, allele 402 becomes activated by the deletion of element 409. Full-length heavy chains can now be expressed with the downstream $C_H$ exons encoded by elements 411 or 412.

Example 3—Repertoire Preservation by Disruption of the H Chain Open Reading Frame with an Exogenous DNA Cassette In this example, transgenic mice are generated carrying two heavy chain alleles that can be switched on or off by site-specific DNA recombination. On one of the two engineered heavy chain alleles, a DNA cassette flanked by two oppositely oriented recognition sequences for a site-specific DNA recombinase is inserted downstream of the J genes but before the switch region preceding the Cµ exons. On the second heavy chain allele, similar elements are inserted at an analogous position, but in the reverse orientation. The DNA cassettes are designed to disrupt the open reading frame of the heavy chain exons when aligned in the same transcriptional orientation as the assembled VDJ exon.

In one specific aspect, the DNA cassettes on both alleles consist of exons 15 and 16 from the murine integrin beta-7 (Itgb7) gene that are flanked by the recognition sequences, lox66 and lox71, for Cre recombinase (see, e.g., Oberdoerffer, et al., Nucleic Acids Research, 31:e140 (2003)). Both Itgb7 exons contain a splice acceptor. Additionally, Itgb7 exon 15 harbors a stop codon, while Itgb7 exon 16 contains another stop codon as well as a poly-adenylation sequence signal. On the allele where this DNA cassette is aligned in the same transcriptional orientation as the VDJ exon, no full-length heavy chain proteins can be expressed due to the premature stop codons and poly-adenylation signal. On the allele where the DNA cassette is inserted in an inverted transcriptional orientation, the DNA cassette does not interfere with heavy chain expression from an in-frame recombined VDJ exon.

In another specific aspect, instead of Itgb7 exons, the DNA cassette that is inserted in the same transcriptional orientation as the $V_H$ exon consists of an open reading frame encoding a gene that provides survival, functional, or selection advantages to the B cells that have successfully assembled an in-frame VDJ exon. An example of such gene is the anti-apoptotic B-cell lymphoma-2 (Bcl2). To prevent this gene from being expressed as a protein fused to the $V_H$ exon, a ribosomal skip sequence such as the 2A peptide from a picornavirus is placed between the splice acceptor and the open reading frame of the advantageous gene. The 2A peptide also ensures that the advantageous gene is only expressed in the B cells that have successfully assembled an in-frame $V_H$ exon, and not in the B cells that lack a productive VDJ rearrangement.

In one exemplary aspect, the assembled VDJ genes on both heavy chain alleles are derived from individual gene segments comprising human coding sequences with mouse regulatory and other non-coding sequences as described in co-pending application US Pub. No. 2013/0219535 by Wabl and Killeen. All endogenous sequences downstream, including the heavy chain constant region genes, are described in LOCUS: NG_005838 (1 . . . 180,971). Sequences of the Itgb7 and Bcl2 DNA cassettes are specified at [SEQ ID Nos. 1 and 2] and are inserted at around position 179,000 of the locus, downstream of the J genes but before the switch region of the first exon Cµ exon.

B cells are able to develop normally as long as they have successfully assembled a productive $V_H$ exon from the heavy chain allele that contains the Itgb7 DNA cassette in an inverted transcriptional orientation. However, if a developing B cell has successfully assembled an in-frame $V_H$ exon on the allele containing the DNA cassette in the same transcriptional orientation, full-length heavy chain proteins cannot be expressed. The developing B cell must move on to assemble a $V_H$ exon on the other allele in order to develop further. The light chains in these B cells are derived from normal independent VJ rearrangements at one of their light chain loci.

Upon expression of a site-specific DNA recombinase, the DNA cassettes on both heavy chain alleles are inverted. The Itgb7 gene cassette previously in the reverse transcriptional orientation to the $V_H$ exon is now aligned in same transcriptional orientation as the $V_H$ exon. In this new orientation, the stop codons and poly-adenylation signal sequence of the Itgb7 gene prevent further expression of full-length heavy chains from this allele, which has formerly supported B cell development and survival. By contrast, the $V_H$ exon of the allele that has been previously prevented from full-length heavy chain expression—and therefore, hidden from tolerance mechanisms—can now generate functional heavy chains because the open reading frame of the inserted DNA cassette is no longer in the same transcriptional orientation as the heavy chain mRNA. In a favored configuration, the Cre recombinase expression is under the control of a CD21 or CD23 promoter.

Following an immunization regimen, hybridoma or other cloning technology are exploited to recover B cells with specificity for the immunogen.

Figure 5:
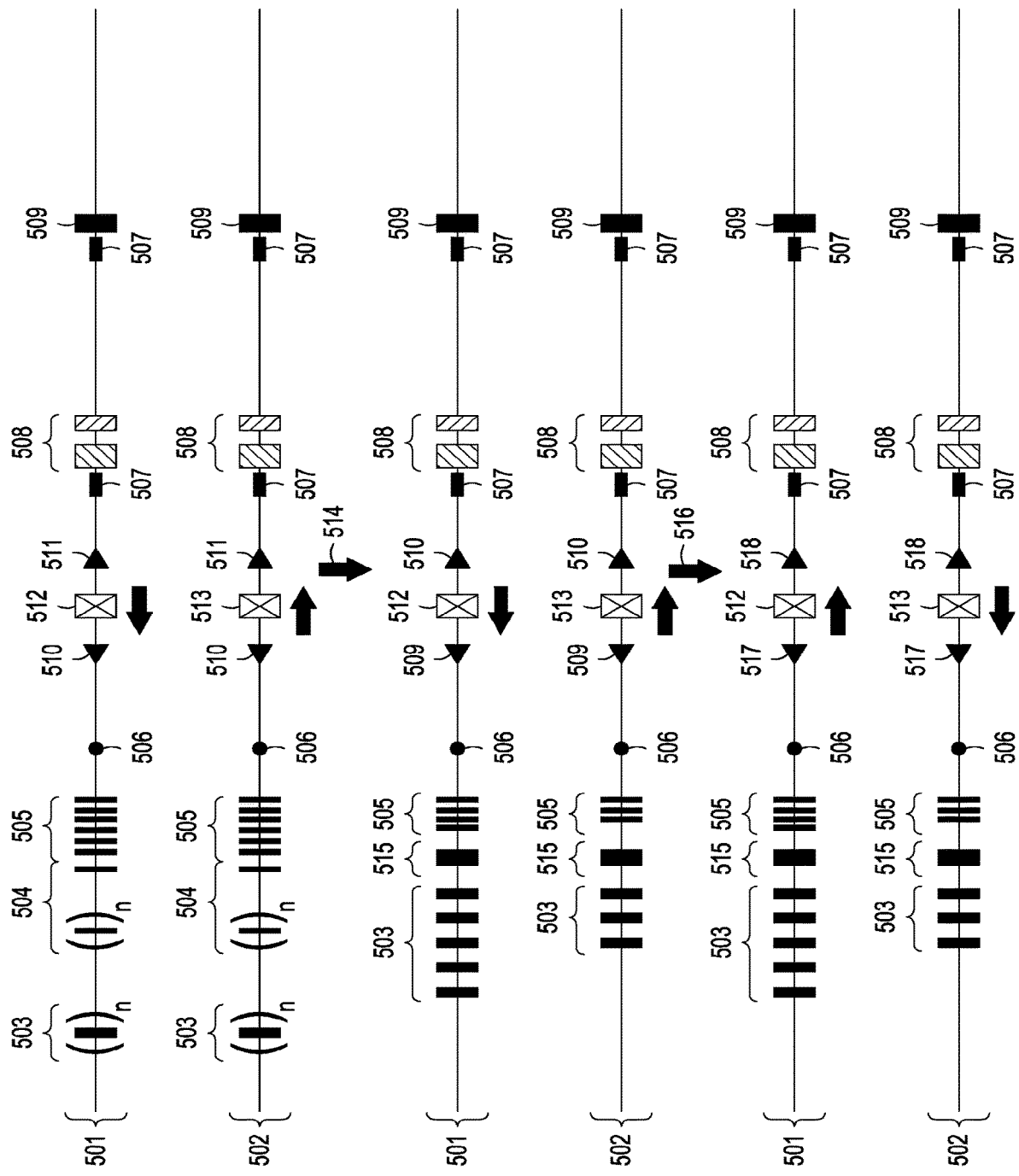
FIG. 5 depicts repertoire preservation of a heavy chain allele via disruption of an open reading frame with an exogenous DNA cassette.

This exemplary version of the embodiment is illustrated in FIG. 5. Shown in this figure are two modified heavy chain alleles (501, 502) containing multiple V (503), D (504), and J (505) genes. The presence of multiple V (503) and D (504) genes is compressed and denoted by "n". On allele 501, a DNA cassette (512) [SEQ ID No. 1] flanked by two oppositely oriented recognition sequences (510, 511) for a site-specific DNA recombinase is inserted downstream of the J genes before the exons encoding Cµ and/or Cδ constant domains (508). This DNA cassette (512) [SEQ ID No. 1] is in reverse orientation relative to the transcriptional direction and contains one or more of the following: a splice acceptor, a ribosomal skip sequence or IRES, an open reading frame, a stop codon, or a poly-adenylation signal sequence. A similar DNA cassette (513) [SEQ ID No. 2] is also inserted at an analogous locale on allele 502, but is in the same sense orientation as the transcriptional direction. After VDJ recombination (514), allele 502 cannot express full-length heavy chains because the DNA cassette (513) [SEQ ID No. 2] disrupts its open reading frame following the VDJ exon (515). By contrast, allele 501 can express full-length heavy chains because the inverted DNA cassette (512) [SEQ ID No. 1] does not disrupt its open reading frame. When expression of the first site-specific DNA recombinase is induced (516), the DNA cassettes on both alleles (512, 513) [SEQ ID Nos. 1 and 2] undergo irreversible inversion because the resultant recombination sites (517, 518) are no longer competent for recombination. Allele 502 is now capable of expressing full-length heavy chains because the DNA cassette (513) [SEQ ID No. 2] is now in reverse orientation and no longer disrupts its open reading frame. By contrast, the open reading frame of allele 501 becomes disrupted by the DNA cassette (512) [SEQ ID No. 1] now in the same orientation as its VDJ exon (515).

Example 4—Repertoire Preservation by Disruption of H Chain Open Reading Frame with a Selection Marker In this example, transgenic mice are engineered to carry two modified heavy chain alleles at the endogenous heavy chain locus.

In a specific aspect of the embodiment, on one heavy chain allele, a $V_H$ exon consisting of preassembled VDJ exon with specificity for a predetermined antigen is inserted upstream of the intronic μ enhancer, where the J genes normally reside. Downstream of the Cμ switch region, in front of the first endogenous Cμ exon, a DNA cassette containing a splice acceptor is inserted to disrupt the open reading frame of mRNA transcribed from the preassembled VDJ exon. In a specific and preferred aspect, the DNA cassette consists of exons 15 and 16 from the murine integrin beta-7 (Itgb7) gene. Both Itgb7 exons contain a splice acceptor. Additionally, Itgb7 exon 15 harbors a stop codon, while Itgb7 exon 16 contains a stop codon as well as a poly-adenylation sequence signal. Flanking the DNA cassette are two directly oriented recognition sequences for a site-specific DNA recombinase, such as loxP for Cre. The endogenous Cμ and Cδ exons for IgM and IgD expression are left intact; however, all elements further downstream including the exons encoding all other isotypes are removed, except for one switch region that is not tethered to any downstream $C_H$ exons.

On the other heavy chain allele, a different DNA cassette containing a splice acceptor is also inserted downstream of the Cμ switch region, around where the first Cμ exon normally resides. In a preferred configuration, this DNA cassette contains an open reading frame encoding a site-specific DNA recombinase that recognizes the recombination sequences flanking the DNA cassette on the other modified heavy chain allele. Additionally, a ribosomal skip sequence such as the 2A peptide from a picornavirus is placed between the splice acceptor and the site-specific recombinase open reading frame. Under this configuration, only an in-frame VDJ rearrangement can lead to expression the site-specific DNA recombinase enzyme. All other elements including the switch regions and exons of other antibody classes are left intact on this allele.

In a favored aspect of the embodiment, the V, D, and J genes to be recombined but prevented from full-length heavy chain expression consist of human coding sequences with mouse regulatory and other non-coding sequences as described in co-pending application US Pub. No. 2013/0219535 by Wabl and Killeen. All endogenous sequences downstream, including the heavy chain constant region genes, are described in LOCUS: NG_005838 (1 . . . 180, 971). Sequences of the Itgb7 and recombinase-encoding DNA cassettes are specified at [SEQ ID Nos. 3 and 5] and are inserted at around position 179,000 and 175,000 of the locus, respectively. The translated amino acid sequence of SEQ ID No. 3 is specified at [SEQ ID No. 4].

A transgenic mouse harboring the two modified heavy chain alleles just described can only generate naïve B cells that express full-length heavy chains from the pre-assembled $V_H$ exon. However, the open reading frame of the pre-assembled $V_H$ exon is disrupted by a DNA cassette, which is removed only when a site-specific DNA recombinase is expressed from the other modified heavy chain allele. In order for this site-specific DNA recombinase to be expressed, a developing B cell must have recombined an in-frame VDJ exon on the allele that is contiguous with the open reading frame of the site-specific DNA recombinase. Therefore, these modified heavy chain configurations allow for the development of only mature B cells that have successfully recombined a $V_H$ exon that is not expressed on the cell surface—and thus, not subjected to purging by tolerance mechanisms.

In a preferred configuration, the pre-assembled VDJ exon encodes a $V_H$ domain that is specific for a hapten, such as the nitrophenol (NP) compound. Alternatively, the pre-assembled VDJ exon may encode a $V_H$ domain that is specific for the $V_H$ domain of another antibody (i.e., an idiotypic antibody). Sequence of the pre-assembled VDJ exon encoding a $V_H$ with specificity against NP is described in Gen-Bank: K00608.1. Sequence of the promoter region upstream of this pre-assembled $V_H$ exon is described in GenBank: M12421.1. The assembled sequence (promoter with pre-assembled VDJ exon) is specified at [SEQ ID No. 6] and inserted around position 181,000 of LOCUS: NG_005838 (where J genes normally reside).

Transgenic mice harboring the modified heavy chain alleles just described are then immunized with the immunogen of interest in combination with the predetermined antigen, which the pre-assembled $V_H$ domain-containing antigen receptors on all naïve B cells can recognize. The predetermined antigen induces isotype switching in the vast majority of activated B cells. As a result, the exons encoding $C_H$ domains of the pre-assembled $V_H$ exon are excised from the chromosome, effectively leading to the inactivation of this heavy chain allele because no other $C_H$ exons exist downstream of the second switch region.

In many B cells, isotype switching will also occur on the second heavy chain allele on which a productive VDJ rearrangement has led to expression of the site-specific recombinase in place of full-length heavy chains. Class switching on this allele removes the recombinase-encoding DNA cassette, allowing for full-length heavy chain expression with downstream exons of Cγ or other isotypes.

Thus, the recombined $V_H$ domain previously hidden from tolerance mechanisms can now directly participate in the germinal center reactions against the immunogen of interest. B cells that have undergone class switching only on the first allele that contains the pre-assembled $V_H$ exon will not survive in germinal centers due to the lack of antigen receptor expression on the cell surface. As a result, only the isotype-switched B cells that have also activated the second heavy chain allele can participate in the germinal center reaction.

Repeated immunizations may be employed to invoke maximal class switching in the activated B cells. Following the immunization regimen, hybridoma or other cloning technology may be exploited to recover class-switched B cells with specificity for the immunogen.

Figure 6:
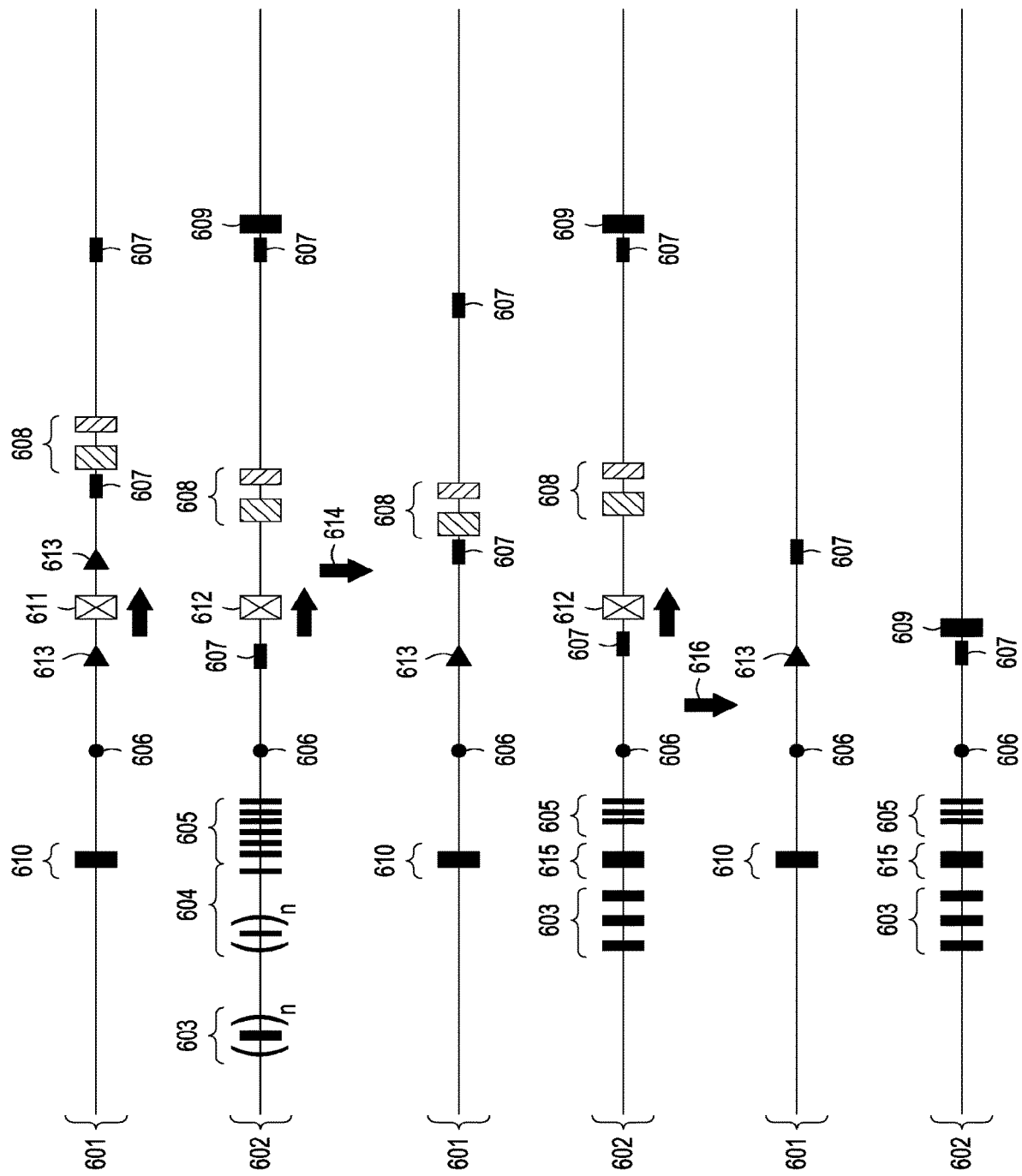
FIG. 6 depicts repertoire preservation of a heavy chain allele via disruption of an open reading frame with a selectable marker.

This example is illustrated in FIG. 6. Shown in this figure are two modified heavy chain alleles (601, 602). On one allele (601), a pre-assembled VDJ exon (610) [SEQ ID No. 3] is inserted upstream of the intronic μ enhancer (606) where J genes normally reside. Downstream of the intronic μ enhancer, a DNA cassette (611) [SEQ ID No. 5] flanked by two directly oriented recognition sequences (613) for a site-specific DNA recombinase is inserted. The DNA cassette contains one or more of the following to disrupt the mRNA open reading frame transcribed from the pre-assembled VDJ exon (610) [SEQ ID No. 3]: a splice acceptor, a ribosomal skip, an open reading frame, a stop codon, or a poly-adenylation signal sequence. Further downstream of the exons encoding Cμ and/or Cδ constant domains (608) on allele 601 is a switch region (607) that is not tethered to any $C_H$-encoding exons. On allele 602, multiple V (603), D (604), and J (605) genes are present for normal VDJ recombination during B cell development. The rest of this allele 602 may be left at its native configuration, except for the insertion of another DNA cassette (612) [SEQ ID No. 6] downstream of the intronic μ switch region (607) and upstream of the Cμ exons (608). This DNA cassette (612) [SEQ ID No. 6] contains a splice acceptor, followed by a ribosomal skip sequence, an open reading frame encoding a site-specific recombinase that can recognize the recombination sequences (613) present on the other heavy chain allele, and a poly-adenylation signal sequence. Thus, B cells can develop only if they have assembled (614) an in-frame VDJ exon (615) on allele 602. Only an in-frame VDJ rearrangement can lead to expression of the site-specific recombinase required to remove the DNA cassette (611) [SEQ ID No. 5] that disrupts the mRNA open reading frame on allele 601. Consequently, all mature naïve B cells express antigenic receptors consisting of the pre-assembled VDJ (610) [SEQ ID No. 3] encoding a $V_H$ specific for a predetermined antigen. Following an antigenic response by the receptors expressed from the preassembled VDJ exon (610) [SEQ ID No. 3], isotype switching (616) results in (i) deletion of the $C_H$ domain-encoding DNA on allele 601 and (ii) deletion of the recombinase-encoding DNA cassette from allele 602. Thus, allele 601 becomes inactivated with the concurrent activation allele 602.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. In the claims that follow, unless the term "means" is used, none of the features or elements recited therein should be construed as means-plus-function limitations pursuant to 35 U.S.C. § 112, ¶6.

We claim:

1. A genetically modified mouse comprising a first immunoglobulin heavy chain allele in which some or all constant domain ($C_H$) exons of the first immunoglobulin heavy chain are flanked by oppositely oriented site-specific recognition sequences and a second immunoglobulin heavy chain allele in which a constant domain ($C_H$) exon of the second immunoglobulin heavy chain allele is in antisense orientation with respect to transcriptional direction and is flanked by oppositely oriented site-specific recognition sequences, wherein the first immunoglobulin heavy chain allele is capable of expressing functional immunoglobulin heavy chain and the second immunoglobulin heavy chain allele can undergo productive VDJ rearrangement but is deficient in expression of a functional immunoglobulin heavy chain, wherein the deficiency in expression of the second allele can be corrected by site-specific recombination to allow for production of a functional immunoglobulin heavy chain that has not been subjected to selection by tolerance mechanisms.

2. The genetically modified mouse of claim 1, wherein the second immunoglobulin heavy chain allele is modified such that in-frame VDJ rearrangement is disabled for allelic exclusion but preserved for expression in an inducible manner.

3. The genetically modified mouse of claim 1, wherein a functional heavy chain cannot be expressed efficiently from the second immunoglobulin heavy chain allele at an immature stage of B cell development following a productive VDJ rearrangement.

4. The genetically modified mouse of claim 1, wherein expression of a productively rearranged VDJ exon that has not been previously expressed as part of a functional heavy chain during an immature stage of B cell development can be induced.

5. The genetically modified mouse of claim 1, wherein a functional heavy chain can be expressed from a productively rearranged VDJ exon of the second immunoglobulin heavy chain allele in or following the presence of a recombinase, DNA-modifying protein, or transcriptional regulator.

6. The genetically modified mouse of claim 1, wherein one or both immunoglobulin heavy chain alleles comprise wild-type or mutated recognition sequences for one or more site-specific recombinases.

7. The genetically modified mouse of claim 1, wherein $C_H$ functionality is switched from the first immunoglobulin heavy chain allele to the second immunoglobulin heavy chain allele by site-specific recombination.

8. The genetically modified mouse of claim 1, wherein expression of a site-specific recombinase is under control of an inducible promoter.

9. The genetically modified mouse of claim 1, wherein expression of a site-specific recombinase is under control of a promoter derived from a gene that is expressed after B cells have matured.

10. The genetically modified mouse of claim 9, wherein the site-specific recombinase is under control of a promoter derived from CD21 or CD23.

11. The genetically modified mouse of claim 1, wherein the first and second immunoglobulin heavy chain allele comprise human immunoglobulin genes.

12. The genetically modified mouse of claim 1, comprising a partially human immunoglobulin region comprising human variable region coding sequences and rodent regulatory and non-coding variable sequences.

* * * * *

SEQUENCE LISTING

```
<160> NUMBER OF SEQ ID NOS: 6

<210> SEQ ID NO 1
<211> LENGTH: 625
<212> TYPE: DNA
<213> ORGANISM: Artificial Sequence
<220> FEATURE:
<223> OTHER INFORMATION: Element 512 in Figure 5, including splice
      acceptor, mouse Itgb7 exon 15 with stop codon, mouse Itgb7 intron,
      mouse Itgb7 exon 15 with stop codon and 3' untranslated region,
      and polyadenylation sequence

<400> SEQUENCE: 1
agggagtgga tcacacccgt gccatcatac tgggctgcac aggggggcatc gtggcagtgg      60 gactagggct ggttctggct tactgactct ctgtggaaat ctacgaccga cgggagtaca     120
ggcgctttga gaaggagcag cagcaactca actgaagca ggtgaggcca gcgactgctg      180
ccacaggctg ggctttcctg gtgacgtctc ttaactttct gtatccctaa cacataacca     240
gctctaaagc ttccccgtgc aagtccctcc ctcggcataa ccaggcctcg gagatctggc     300
ctcgtggggc aggtagtggg gagagcctga tagtttttcct tactgtgtgc aatgttttcc    360
cacaggacaa caatcctctc tacaaaagtg cgatcacaac cactgtcaac ccccgcttcc     420
```

```
aagggacaaa cggtcggtcg ccatccctct ctctgaccag ggaagcagac tgacttagga        480
ttcttgtctt ggaggacagt ggagatagaa gggcagggca gcgtctgtca ggcaaagatg        540
ctgccaccgc tgagattttt cagagtgacc ttcagagggc agcagccatt cccaccacac        600
gaagggctgg tccttccata ataaa                                              625

<210> SEQ ID NO 2
<211> LENGTH: 760
<212> TYPE: DNA
<213> ORGANISM: Artificial Sequence
<220> FEATURE:
<223> OTHER INFORMATION: Element 513 in Figure 5: splice acceptor,
      linker, PTV1-2A peptide, mouse Bcl2 open reading frame, 3'
      untranslated region, polyadenylation sequence

<400> SEQUENCE: 2 caggggatc cggagccacg aacttctctc tgttaaagca agcaggagac gtggaagaaa          60
accccggtcc tatggcgcaa gccgggagaa cagggtatga taaccgggag atcgtgatga        120
agtacataca ttataagctg tcacagaggg gctacgagtg ggatgctgga gatgcggacg        180
cggcgcccct gggggctgcc cccaccctg gcatcttctc cttccagcct gagagcaacc        240
caatgcccgc tgtgcaccgg gacatggctg ccaggacgtc tcctctcagg cccctcgttg        300
ccaccgctgg gcctgcgctc agccctgtgc cacctgtggt ccatctgacc ctccgccggg        360
ctggggatga cttctctcgt cgctaccgtc gtgacttcgc agagatgtcc agtcagctgc        420
acctgacgcc cttcaccgcg aggggacgct tgccacggt ggtggaggaa ctcttcaggg        480
atggggtgaa ctgggggagg attgtggcct tctttgagtt cggtgggggtc atgtgtgtgg        540 agagcgtcaa caggagatg tcaccctgg tggacaacat cgccctgtgg atgactgagt        600
acctgaaccg gcatctgcac acctggatcc aggataacgg aggctgggta ggtgcatgtc        660
tggttgaatg agtctgggct ttgatctcaa ggccaagatg cgcaggttgg ggtgtgagtg        720
gattctgggt caaatgggc cattgagcag atgaaataaa                               760

<210> SEQ ID NO 3
<211> LENGTH: 699
<212> TYPE: DNA
<213> ORGANISM: Artificial Sequence
<220> FEATURE:
<223> OTHER INFORMATION: Element 610 in Figure 6: promoter and other
      regulatory sequences, exon 1, intron, exon 2.

<400> SEQUENCE: 3
ggatccagag ttaggacttg gactgactca ggaggactct agtttcttct tctccagctg         60
gaatgtcctt atgtaagaaa agccttgcct catgagtatg caaatcatgt gcgactgtga        120
tgattaatat agggatatcc acaccaaaca tcatatgagc cctatcttct ctacagacac        180
tgaatctcaa ggtccttaca atgaaatgca gctgggttat cttcttcctg atggcagtgg        240
ttacagggaa ggggctccca agcccaaact tgaggtgtcc ataaactctc tgtgacagtg        300
gcaatccact ttgcctttct ttctacaggg gtcaattcag aggttcagct gcagcagtct        360
ggggcagagc ttgtgaggcc aggggcctca gtcaagttgt cctgcacggc ttctggcttc        420
aacattaaag acacctatat gcactgggtg aagcagaggc ctgaacaggg cctggagtgg        480
attggaagga ttgatcctgc gaatggtaat actaaatatg acccgaagtt ccagggcaag        540
gccactataa cagcagacac atccaccaac acagcctacc tgcagctcag cagcctgaca        600
```

```
tctgaggaca ctgccgtcta ttactgtgct agatactata ggtacccta ctatgctatg        660 gactactggg gtcaaggaac ctcagtcacc gtctcctca                              699
```

<210> SEQ ID NO 4
<211> LENGTH: 139
<212> TYPE: PRT
<213> ORGANISM: Artificial Sequence
<220> FEATURE:
<223> OTHER INFORMATION: Translated amino acid sequence of element 610
      in Figure 6

<400> SEQUENCE: 4

```
Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Arg
            20                  25                  30

Pro Gly Ala Ser Val Lys Leu Ser Cys Thr Ala Ser Gly Phe Asn Ile
        35                  40                  45

Lys Asp Thr Tyr Met His Trp Val Lys Gln Arg Pro Glu Gln Gly Leu
    50                  55                  60

Glu Trp Ile Gly Arg Ile Asp Pro Ala Asn Gly Asn Thr Lys Tyr Asp
65                  70                  75                  80

Pro Lys Phe Gln Gly Lys Ala Thr Ile Thr Ala Asp Thr Ser Thr Asn
                85                  90                  95

Thr Ala Tyr Leu Gln Leu Ser Ser Leu Thr Ser Glu Asp Thr Ala Val
            100                 105                 110

Tyr Tyr Cys Ala Arg Tyr Tyr Arg Tyr Pro Tyr Tyr Ala Met Asp Tyr
        115                 120                 125

Trp Gly Gln Gly Thr Ser Val Thr Val Ser Ser
    130                 135
```

<210> SEQ ID NO 5
<211> LENGTH: 627
<212> TYPE: DNA
<213> ORGANISM: Artificial Sequence
<220> FEATURE:
<223> OTHER INFORMATION: Sequence of DNA cassette, element 611 in Figure
      6: splice acceptor, mouse Itgb7 exon 15 with stop codon, mouse
      Itgb7 intron, mouse Itgb7 exon 15 with stop codon followed by 3'
      untranslated region, polyadenylation sequence

<400> SEQUENCE: 5

```
cagagggagt ggatcacacc cgtgccatca tactgggctg cacaggggc atcgtggcag        60 tgggactagg gctggttctg gcttactgac tctctgtgga aatctacgac cgacgggagt       120
acaggcgctt tgagaaggag cagcagcaac tcaactggaa gcaggtgagg ccagcgactg       180
ctgccacagg ctgggctttc ctggtgacgt ctcttaactt tctgtatccc taacacataa       240
ccagctctaa agcttccccg tgcaagtccc tccctcggca taaccaggcc tcggagatct       300
ggcctcgtgg ggcaggtagt ggggagagcc tgatagtttt ccttactgtg tgcaatgttt       360
tcccacagga caacaatcct ctctacaaaa gtgcgatcac aaccactgtc aaccccgct        420 tccaagggac aaacggtcgg tcgccatccc tctctctgac cagggaagca gactgactta       480
ggattcttgt cttggaggac agtggagata gaagggcagg gcagcgtctg tcaggcaaag       540
atgctgccac cgctgagatt tttcagagtg accttcagag ggcagcagcc attcccacca       600
cacgaagggc tggtccttcc ataataa                                           627
```

```
<210> SEQ ID NO 6
<211> LENGTH: 1393
<212> TYPE: DNA
<213> ORGANISM: Artificial Sequence
<220> FEATURE:
<223> OTHER INFORMATION: Sequence of DNA cassette, element 612 in Figure
      6: splice acceptor, PDGFR transmembrane domain, linker, PTV1-2A
      peptide; Cre recombinase coding sequence, 3' untranslated region
      with poly-A signal

<400> SEQUENCE: 6
caggggctgt gggccaggac acgcaggagg tcatcgtggt gccacactcc ttgcccttta      60
aggtggtggt gatctcagcc atcctggccc tggtggtgct caccatcatc tcccttatca     120
tcctcatcat gctttggcag aagaagccac gtatgtccaa tttactgacc gtacaccaaa     180
atttgcctgc attaccggtc gatgcaacga gtgatgaggt tcgcaagaac ctgatggaca     240
tgttcaggga tcgccaggcg ttttctgagc atacctggaa aatgcttctg tccgtttgcc     300
ggtcgtgggc ggcatggtgc aagttgaata accggaaatg gtttcccgca gaacctgaag     360
atgttcgcga ttatcttcta tatcttcagg cgcgcggtct ggcagtaaaa actatccagc     420
aacatttggg ccagctaaac atgcttcatc gtcggtccgg gctgccacga ccaagtgaca     480
gcaatgctgt ttcactggtt atgcggcgga tccgaaaaga aaacgttgat gccggtgaac     540
gtgcaaaaca ggctctagcg ttcgaacgca ctgatttcga ccaggttcgt tcactcatgg     600
aaaatagcga tcgctgccag gatatacgta atctggcatt tctggggatt gcttataaca     660
ccctgttacg tatagccgaa attgccagga tcagggttaa agatatctca cgtactgacg     720
gtgggagaat gttaatccat attggcagaa cgaaaacgct ggttagcacc gcaggtgtag     780
agaaggcact tagcctgggg gtaactaaac tggtcgagcg atggatttcc gtctctggtg     840
tagctgatga tccgaataac tacctgtttt gccgggtcag aaaaaatggt gttgccgcgc     900
catctgccac cagccagcta tcaactcgcg ccctggaagg gattttttgaa gcaactcatc     960 gattgattta cggcgctaag gatgactctg gtcagagata cctggcctgg tctgacacag    1020
gtgcccgtgt cggagccgcg cgagatatgg cccgcgctgg agtttcaata ccggagatca    1080
tgcaagctgg tggctggacc aatgtaaata ttgtcatgaa ctatatccgt aacctggata    1140
gtgaaacagg ggcaatggtg cgcctgctgg aagatggcga ttagagacaa aggtcctgag    1200
acgccaccac cagctcccca gctccatcct atcttccctt ctaaggtctt ggaggcttcc    1260
ccacaagcga cctaccactg ttgcggtgct ccaaacctcc tccccacctc cttctcctcc    1320
tcctcccttt ccttggcttt tatcatgcta atatttgcag aaaatattca ataaagtgag    1380
tctttgcact tga                                                       1393
```